United States Patent [19]
Thompson

[11] Patent Number: 6,091,987
[45] Date of Patent: Jul. 18, 2000

[54] POWER CONSUMPTION REDUCTION IN MEDICAL DEVICES BY EMPLOYING DIFFERENT SUPPLY VOLTAGES

[75] Inventor: David L. Thompson, Fridley, Minn.

[73] Assignee: Medtronic, Inc., Minneapolis, Minn.

[21] Appl. No.: 09/181,459

[22] Filed: Oct. 28, 1998

Related U.S. Application Data

[63] Continuation-in-part of application No. 09/067,881, Apr. 29, 1998, abandoned.

[51] Int. Cl.$^7$ .................................................. A61N 1/00
[52] U.S. Cl. ............................................................. 607/2
[58] Field of Search ............................. 607/2, 9, 5, 29, 607/33, 34

[56] References Cited

U.S. PATENT DOCUMENTS

| | | |
|---|---|---|
| 4,031,899 | 6/1977 | Renirie . |
| 4,460,835 | 7/1984 | Masuoka . |
| 4,561,442 | 12/1985 | Vollmann et al. . |
| 4,791,318 | 12/1988 | Lewis et al. . |
| 5,022,395 | 6/1991 | Russie . |
| 5,154,170 | 10/1992 | Bennett et al. . |
| 5,185,535 | 2/1993 | Farb et al. . |
| 5,388,578 | 2/1995 | Yomtov et al. . |
| 5,610,083 | 3/1997 | Chan et al. . |

OTHER PUBLICATIONS

Jan Mulder et al., "Application of the Back Gate in MOS Weak Inversion Translinear Circuits," IEEE Transactions on Circuits and Systems—I: Fundamental Theory and Applications, vol. 42, No. 11, Nov. 1995.

*Primary Examiner*—Scott M. Getzow
*Attorney, Agent, or Firm*—Thomas F. Woods; Harold R. Patton

[57] ABSTRACT

Power consumption in medical devices is reduced through the application of different supply voltages to analog and digital circuits, respectively. The medical device generally includes analog circuits (e.g., an atrial sense amplifier, a ventricular sense amplifier, a T-wave amplifier, bandpass filters, detection circuits, sensor amplification circuits, physiological signal amplification circuits, output circuits, a battery monitor circuit, and a power on reset circuit) and digital circuits (e.g., a processor, a controller, and a memory) with the supply voltage applied to the analog circuits being greater than that applied to the digital circuits. A source applies a first fixed supply voltage to the digital circuits of the medical device and a voltage generation circuit (e.g., a charge pump circuit) having the first fixed supply voltage applied thereto is used for generating a second fixed supply voltage to be applied to analog circuits of the medical device.

26 Claims, 13 Drawing Sheets

POWER CONSUMPTION REDUCTION IN MEDICAL DEVICES BY EMPLOYING DIFFERENT SUPPLY VOLTAGES

CLAIM TO PRIORITY AND REFERENCE TO RELATED APPLICATION

This application is a Continuation-In-Part, and claims priority and other benefits from the filing date, of U.S. patent application Ser. No. 09/067,881 for "Power Consumption Reduction in Medical Devices Using Multiple Supply Voltages and Clock Frequency Control" to Thompson, filed Apr. 29, 1998, now abandoned, hereby incorporated by reference herein in its entirety.

FIELD OF THE INVENTION

The present invention relates to power consumption of integrated circuit designs such as circuits used in medical devices, particularly implantable devices. More particularly, the present invention pertains to providing different supply voltages for analog and digital circuitry to achieve a reduction in power consumption.

BACKGROUND OF THE INVENTION

Various devices require operation with low power consumption. For example, hand-held communication devices require such low power consumption and, in particular, implantable medical devices require low power capabilities. With respect to implantable medical devices, for example, microprocessor-based implantable cardiac devices, such as implantable pacemakers and defibrillators, are required to operate with a lower power consumption to increase battery life and device longevity.

Generally, such low power devices are designed using complementary metal oxide semiconductor (CMOS) technology. CMOS technology is generally used because such technology has the characteristic of substantially zero "static" power consumption.

The power consumption of CMOS circuits consists generally of two power consumption factors, namely "dynamic" power consumption and static power consumption. Static power consumption is only due to current leakage as the quiescent current of such circuits is zero. Dynamic power consumption is the dominant factor of power consumption for CMOS technology. Dynamic power consumption is basically due to the current required to charge internal and load capacitances during switching, i.e., the charging and discharging of such capacitances. Dynamic power (P) is equal to: $\frac{1}{2}CV_{DD}^2F$, where C is nodal capacitance, F is the clock or switching frequency, and $V_{DD}$ is the supply voltage for the QMOS circuit. As can be seen from the formula for calculating dynamic power (P), such dynamic power consumption of CMOS circuits is proportional to the square of the supply voltage ($V_{DD}$). In addition, dynamic power (P) is proportional to switching or clock frequency (F).

In accordance with the formula for dynamic power consumption, it has been effective conventionally in CMOS integrated circuit designs to scale down the supply voltage for an entire device (e.g., hybrid) or integrated circuit (IC), i.e., operate the circuit at low supply voltages, to reduce power consumption for such designs. For example, in the MEDTRONIC SPECTRAX® device of circa 1979. It, circuitry was powered by one lithium iodine cell (as opposed to the two cells employed in the prior art). This reduced the supply voltage to 2.8 volts from 5.6 volts, thus reducing overhead current. Voltages required to be greater than 2.8 volts were generated by a voltage doubler, or alternatively by a charge pump (E.g., output pacing pulses). Further, for example, in the MEDTRONIC SYMBIOS® device of circa 1983, the logic circuitry was powered by a voltage regulator controlling the IC supply voltage to a "sum of thresholds" supply. This regulator provided a supply to the IC (i.e., $V_{DD}$) of several hundred millivolts above the sum of the n-channel and p-channel thresholds of the CMOS transistors making up the IC. This regulator was self calibrating regarding manufacturing variations of the transistor thresholds.

Other devices have reduced power consumption in other varied manners. For example, various device designs have shut-down analog blocks and/or shut-off clocks to logic blocks not being used at particular times, thereby reducing power. Further, for example, microprocessor based devices have historically used a "burst clock" design to operate a microprocessor at a very high clock rate (e.g., generally 500–1000 Kilohertz (KHz)), for relatively short periods of time to gain the benefit of a "duty cycle" to reduce average current drain. A much lower frequency clock (e.g., generally 32 KHz) is used for other circuitry and/or the processor when not in the high clock rate mode, i.e., burst clock niode. Many known processor based implanted devices utilize the burst clock technique. For example, implanted devices available from Medtronic, Vitatron, Biotronic, ELA, Intermedics, Pacesetters, InControl, Cordis, CPI, etc., utilize burst clock techniques. A few illustrative examples which describe the use of a burst clock are provided in U.S. Pat. No. 4,561,442 to Vollmann et al., entitled "Implantable Cardiac Pacer With Discontinuous Microprocessor Programmable Anti Tachycardia Mechanisms and Patient Data Telemetry," Is issued Dec. 31, 1985; U.S. Pat. No. 5,022,395 to Russie, entitled "Implantable Cardiac Device With Dual Clock Control of Microprocessor," issued Jun. 11, 1991; U.S. Pat. No. 5,388,578 to Yomtov et al., entitled "Improved Electrode System For Use With An Implantable Cardiac Patient Monitor," issued Feb. 14, 1995; and U.S. Pat. No. 5,154,170 to Bennett et al., entitled "Optimization for Rate Responsive Cardiac Pacemaker," issued Oct. 13, 1992.

FIG. 1 represents a graphical illustration of energy/delay versus supply voltage for CMOS circuits such as a CMOS inverter 10 shown in FIG. 2 for illustrative purposes. The inverter 10 is provided with a supply voltage, $V_{DD}$, which is connected to the source of a PMOS field effect transistor (FET) 12. PMOS FET 12 has its drain connected to the drain of an NMOS FET 14 whose source is connected to ground. In this configuration, an input $V_i$ applied to both the gates of FETs 12, 14 is inverted to provide output $V_o$. Simply stated, one clock cycle, or logic level change, is used to invert the input $V_i$ to $V_o$.

As shown in FIG. 1, the circuit logic delay increases drastically as the supply voltage is reduced to near one volt, as represented by delay line 16 and energy/delay line 18. As such, reducing of the supply voltage ($V_{DD}$) continuously to lower levels is impractical because of the need for higher supply voltages when higher frequency operation is required. For example, generally CMOS logic circuits must periodically provide functionality at a higher frequency, e.g., burst clock frequency. However, as the supply voltage ($V_{DD}$) is decreased, such energy consumption is reduced by the square of the supply voltage ($V_{DD}$) as is shown by energy consumption line 20. Therefore, speed requires a higher supply voltage ($V_{DD}$) which is in direct conflict with low power consumption.

Other problems are also evident when lower supply voltages ($V_{DD}$) are used for CMOS circuit designs. When a lower supply voltage is selected, static leakage current losses may arise, particularly at lower frequencies, due to increase(d static leakage current losses.

Various techniques for reducing power consumption in devices are known in the art, some examples of which may be found in the references listed in Table 1 below.

TABLE 1

| U.S. Pat. No. | Inventor | Issue Date |
|---|---|---|
| 4,031,899 | Renirie | 28 June 1977 |
| 4,460,835 | Masuoka | 17 July 1984 |
| 4,561,442 | Vollmann et al. | 31 December 1985 |
| 4,791,318 | Lewis et al. | 13 December 1988 |
| 5,022,395 | Russie | 11 June 1991 |
| 5,154,170 | Bennett et al. | 13 October, 1992 |
| 5,185,535 | Farb et al. | 9 February 1993 |
| 5,388,578 | Yomtov et al. | 14 February 1995 |
| 5,610,083 | Chan et al. | 11 March 1997 |

All references listed in Table 1 above are hereby incorporated by reference herein, each in its respective entirety. As those of ordinary skill in the art will appreciate readily upon reading the Summary of the Invention, Detailed Description of the Embodiments, and claims set forth below, at least some of the devices and methods disclosed in the publications, patents or patent applications referenced in the present application, including those disclosed in the references listed in Table 1 above, may be modified advantageously in accordance with the teachings of the present invention.

SUMMARY OF THE INVENTION

The present invention has certain objects. That is, various embodiments of the present invention provide solutions to one or more problems existing in the prior art respecting circuitry design having lower power consumption, particularly with respect to implantable medical devices. Those problems include: CMOS, CML, SOS, SOI, BICMOS, PMOS and/or NMOS circuits having excessive dynamic power consumption which reduces battery life; the inability to utilize low voltage supply levels effectively; and lack of ability to provide adequate processing capabilities such as high processing capabilities including telemetry uplink/downlink, morphology detection, initialization of devices, while still providing low processing capabilities such as sensing intrinsic beats, pacing, low speed telemetry, with the desired power consumption.

In comparison to known techniques for reducing power consumption in circuit designs, various embodiments of the present invention may provide one or more of the following advantages: reduced power consumption through the use of a lower voltage supply ($V_{DD}$) for digital circuitry; increased longevity of circuits, particularly implantable device circuitry; provide a potential reduction in product size; minimize static leakage current losses, i.e., static power consumption; provide multi-processor designs, DSP designs, and high performance processing designs with additional features/function opportunities due to tine ability to reduce power with respect to other "required" features and functions; and provide for substantial reduction in current drain for the overall design even when operating analog circuitry at higher supply voltages relative to the supply voltages applied to digital circuitry of the design.

Some embodiments of the invention include one or more of the following features: one or more analog circuits of a medical device (e.g., an atrial sense amplifier, a ventricular sense amplifier, a T-wave amplifier, one or more bandpass filters, one or more detection circuits, one or more sensor amplification circuits, one or more physiological signal amplification circuits, one or more output circuits, a battery monitor circuit, and/or a power on reset circuit) and one or more digital circuits of the medical device (e.g., a processor, a controller and/or a memory) with the supply voltage applied to the analog circuits being greater than that applied to the digital circuits; a source for applying a first fixed supply voltage to digital circuits of a medical device and a voltages generation circuit (e.g., a charge pump circuit) having the first fixed supply voltage applied thereto for generating a second fixed supply voltage to be applied to analog circuits of the medical device; adjustment of back gate bias of digital circuits of the medical device; level shifting of signals being communicated between analog circuits and digital circuits having different supply voltages applied thereto; and employing various ones or combinations of the foregoing features in CMOS, CML (Current Mode Logic), SOS (Silicon on Sapphire), SOI (Silicon on Insulator), BICMOS, PMOS and/or NMOS circuitry.

DETAILED DESCRIPTION OF THE EMBODIMENTS

The present invention is first described with reference to FIGS. 1–14. More particularly, use of different supply voltages for analog and digital circuits according to the present invention is described with reference to FIGS. 12 through 14.

Figure 1:
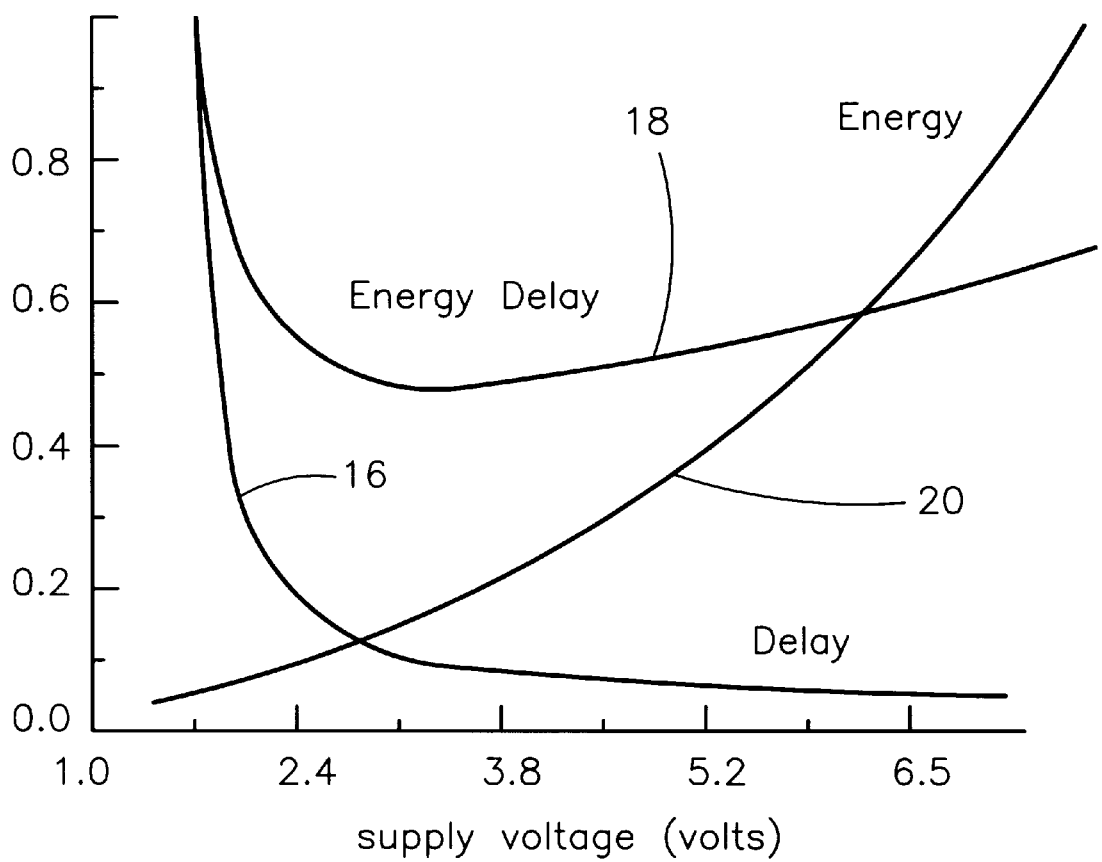
FIG. 1 is a graphical illustration showing energy/delay versus supply voltage for CMOS circuit operation.
Figure 2:
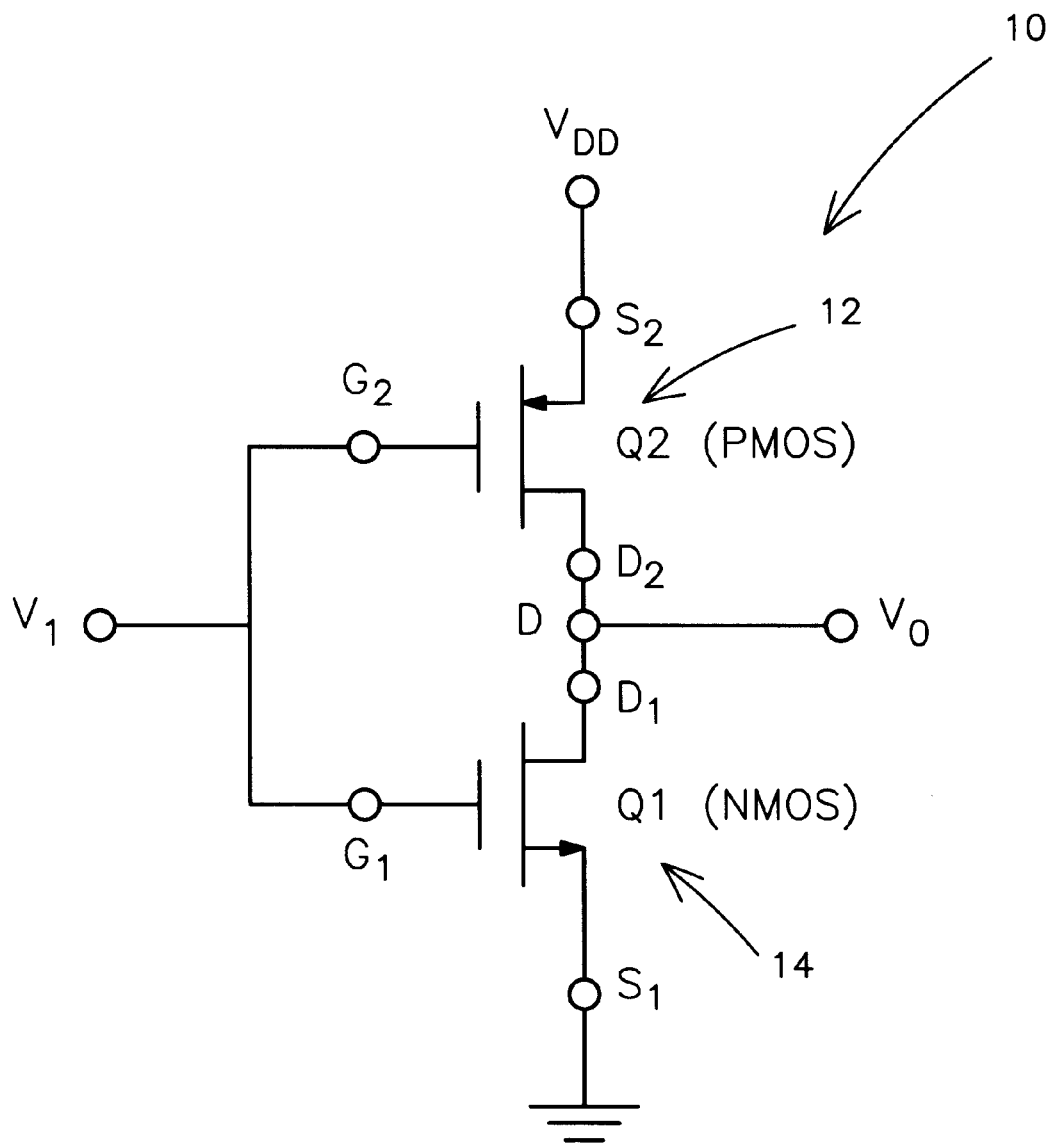
FIG. 2 shows a prior art CMOS inverter which is used as a building block in many CMOS circuit designs.
Figure 3:
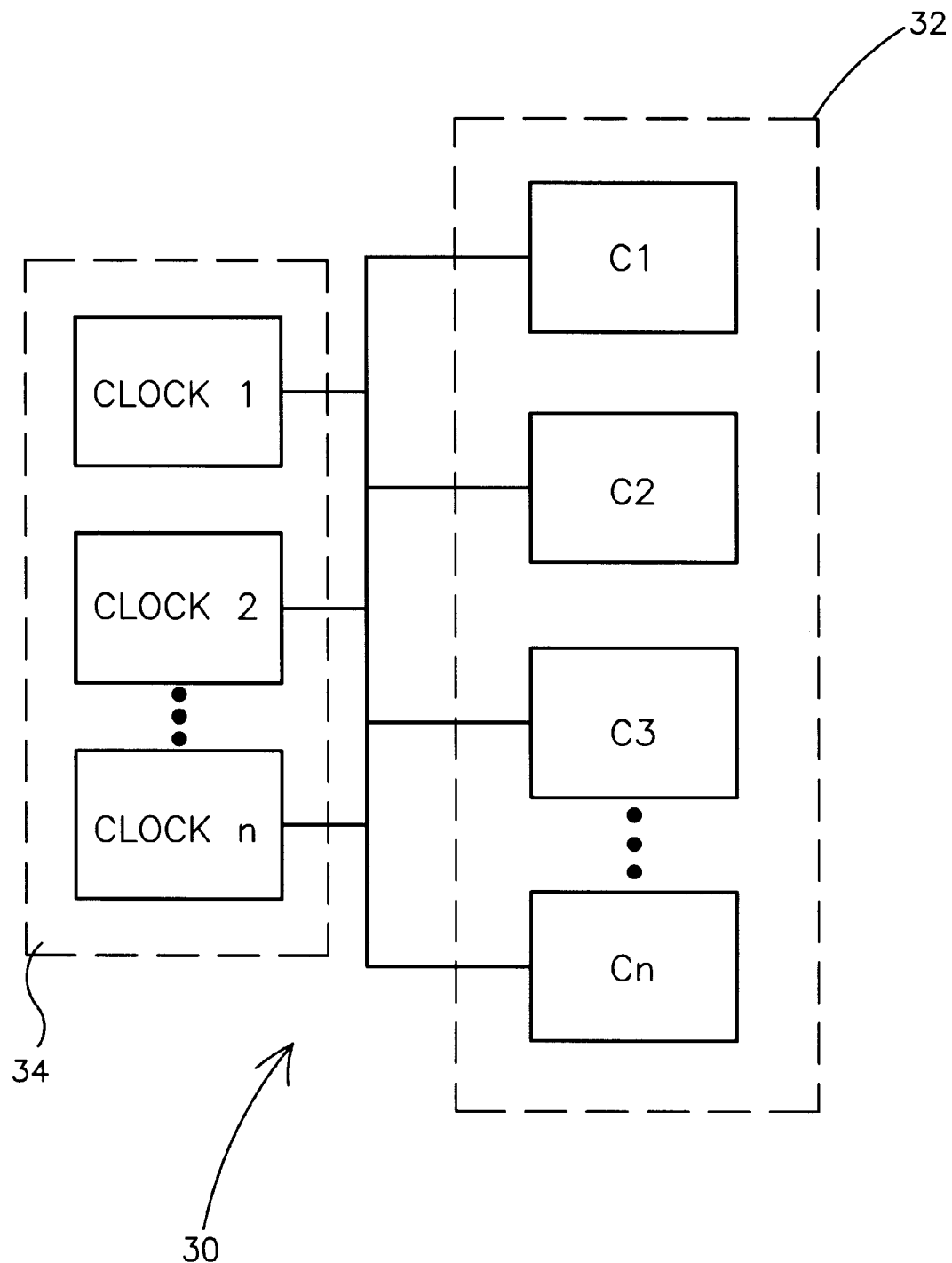
FIG. 3 is a block diagram of a just-in-time clocking system according to the present invention.

FIG. 3 shows a general block diagram of a just-in-time clock system 30. The just-in-time clock system 30 includes an integrated circuit 32 and a clock source 34. The integrated circuit 32 includes a plurality of circuits C1–Cn. Each circuit when operable is capable of performing one or more circuit functions. A function is defined as any operation performed on one or more inputs in a plurality of cycles resulting in an output. Generally, the functions performed by the various circuits C1–Cn are performed in a predetermined number of clock cycles, Clock source 34 is operable for providing clock signals at a plurality of clock frequencies generally shown as clock1–clockn.

The circuits C1–Cn of integrated circuit 32 may include discrete function circuits (i.e., logic circuits for operating upon one or more inputs to implement a particular function to provide one or more outputs therefrom), such as circuits operating on one input from a sensor to provide a representative signal to further functional circuitry, transceiver circuitry, conversion circuitry, etc. Further, the circuits C1–Cn may be data processing circuitry capable of performing multiple functions under program control or such circuits C1–Cn may implement firmware (software) functions/routines that must complete prior to some succeeding event or prior to the start of the next function. For example, as described further herein with respect to illustrative embodiments of implantable medical devices, such circuits may include digital signal processing circuits circuitry used for telemetry uplink/downlink, morphology detection circuitry, arrhythmia detection circuitry, monitoring circuitry, pacing circuitry, microprocessors, etc.

The functions performed by each of the circuits C1–Cn are typically required to be completed in a particular time period prior to a next functional process being undertaken. For example, one logic circuit may perform a function in a predetermined time period to provide an output required by another circuit, or for example, a function may need to be performed by processing circuitry during a particular period of time due to the need for other processing to be performed by such processing circuitry. For example, in an implantable medical device, processing to complete a particular function may need to be performed in a portion of a particular time interval such as a blanking interval, an upper rate interval, an escape interval, or refractory interval of a cardiac cycle, or further, such as during a pulse generator/programmer handshake.

Clock source 34 may be configured in any manner for providing clock signals at a plurality of frequencies. Such a clock source may include any number of clock circuits wherein each provides a single clock signal at a particular frequency, the clock source 34 may include one or more adjustable clock circuits for providing clock signals over a continuous range of clock frequencies, and/or the clock source 34 may include a clock circuit that is operable to provide clock signals at discrete clock frequencies as opposed to over a continuous range. For example, the clock source 34 may include oscillators, clock dividers, timers, clock control circuitry or any other circuit elements required for providing clock signaling according to the present invention. Preferably, the clock source 34 is configured as a continuously oscillating low frequency clock and a controllable on/off higher frequency clock.

Figure 4A:
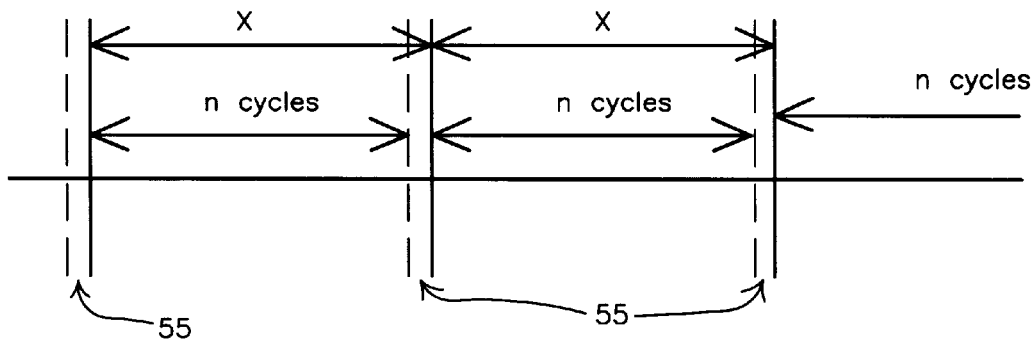
FIGS. 4A–4C show timing illustrations for use in describing the just-in-time decking system of FIG. 3.
Figure 4B:
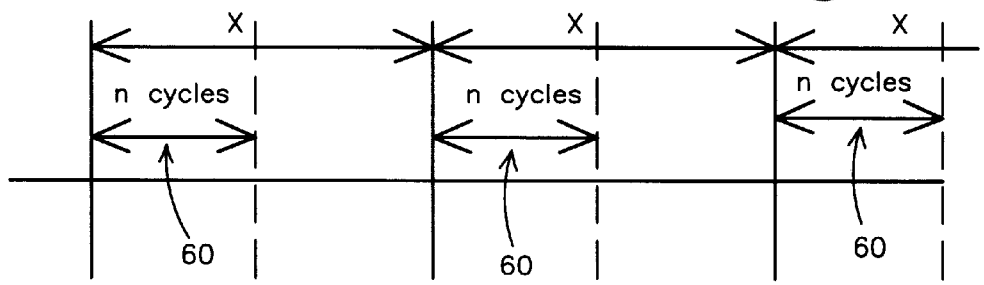
Figure 4C:
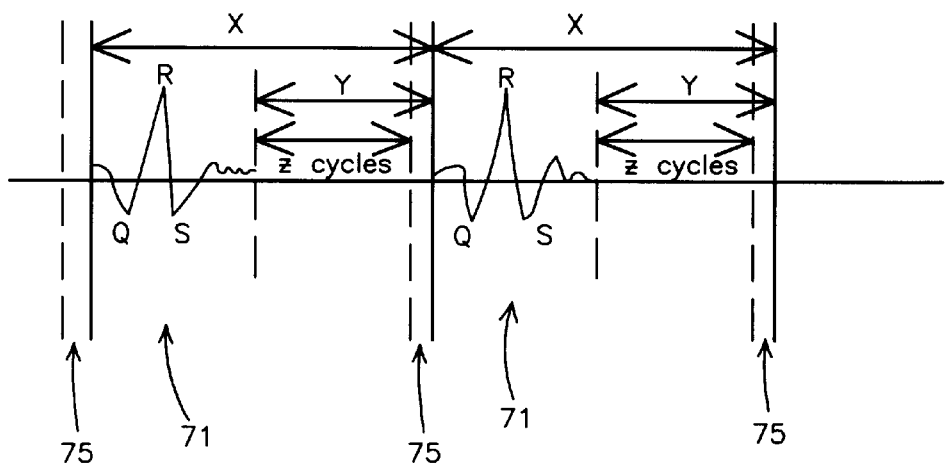

Just-in-time controllable clock operation of the just-in-time clocking system 30 of FIG. 3 is described herein with reference to FIGS. 4A through 4C. As shown in FIG. 4A, time period (x) represents the time period in which a circuit, e.g., one of circuits C1–Cn, is required to complete one or more functions. The same time period (x) is shown in FIG. 4B. The time period x may be equated to any number of different time periods. For example, the time period may be the amount of time a processing circuit has to perform a particular detection function due to the need for a detection output by a certain point in time, may be a time period required to complete a particular function by a certain logic circuit so as to provide a timely output to a digital signal processing circuit, may be a time period to complete a firmware (software) routine, etc. Moreover, the time period x may correspond to a cardiac cycle or a part thereof.

As shown in FIG. 4B, and according to conventional processing techniques, circuit functions are typically performed at a burst cycle frequency and, as; such, the function performed requires a time period 60. Only a small amount of time (e.g., time period 60) of the entire time period x is used to perform the one or more functions requiring n cycles of time to complete. In such a case, conventional burst clocks operate at a high clock rate (e.g., 500–1000 KHz) for such short periods of time to gain the benefit of a "duty cycle" to reduce average current drain. Such high clock rates, however, may not be require for carrying out such functions, or all functions.

With just-in-time clocking according to the present invention, and as shown in FIG. 4A, substantially the entire time period x is used to perform the one or more functions which are completed in n cycles. In other words, the clock frequency (e.g., one of clock1–clockn) for the circuit performing the one or more functions during the time period x is set such that the one or more functions are completed in the maximum time available for performing such functions. In other words, the clock frequency is at its lowest possible value. Stated differently, a lower frequency clock is used such that the one or more functions are performed just-in-time for other circuit or routine functionality to be performed.

In such a just-in-time manner, the clock frequency used to control the performance of such functions by the particular CMOS, CML, SOS, SOI, BICMOS, PMOS and/or NMOS circuitry is lowered resulting in reduced power consumption by the circuitry. According to dynamic power calculations, a lower frequency results in proportional power reduction. With the lowering of the clock frequency, integrated circuit 32 including the various circuits C1–Cn may be designed to operate at a lower frequency (as, for example, opposed to a burst frequency), and also may operate at various other frequencies depending upon need.

It is preferred that substantially the entire predetermined period of time be used so that the one or more functions being performed are completed prior to the end of the time period x (as, for example, represented by remainder time periods 55 in FIG. 4A). Remainder time period 55, for example, is preferably near or about 0 seconds.

FIG. 4C shows an illustrative timing example for processing circuitry which performs multiple functions. The cardiac cycle of a patient is represented in FIG. 4C as time period x. During time period 71 (e.g., during a QRS complex of the cardiac cycle), high speed processing is performed at a high clock frequency in respect of a lower clock frequency employed to control operation of the processing circuitry during time period y. During time period y, when processing circuitry is operated at a lower clock frequency, the lower clock frequency may be set such that the functions performed during z cycles are performed over substantially the entire maximum time period available for such processing (i.e., time period y). Once again, a small remainder time period 75 of the cardiac cycle time period x may exist. Such time period may be, for example, in the range of about 1.0 millisecond to about 10.0 milliseconds when the cardiac cycle is in the range of about 400 milliseconds to about 1200 milliseconds.

Figure 5:
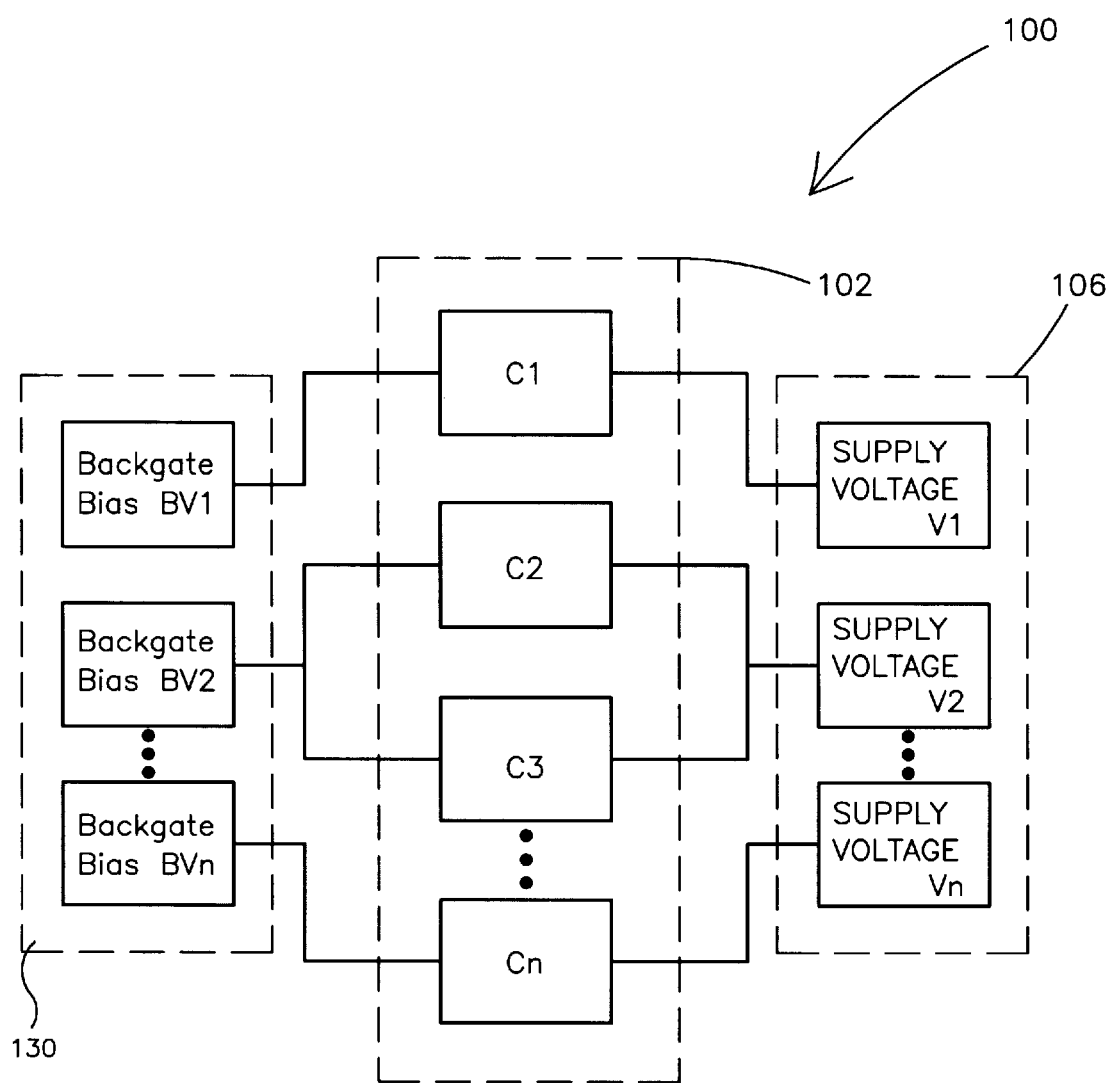
FIG. 5 is a block diagram illustration of a multiple supply voltage system according to the present invention.

FIG. 5 shows a general block diagram of a multiple supply voltage system 100 wherein one or more supply voltages are available, and are tailored for application to various circuits in an IC. The multiple supply voltage system 100 includes integrated circuit 102 and supply voltage source 106. Integrated circuit 102 includes circuits C1–Cn. Supply voltage source 106 is operable for providing a plurality of supply voltages V1–Vn. Each supply voltage from supply voltage source 106 is tailored to be applied to one or more circuits of circuits C1–Cn. As illustrated, supply voltage V1 is applied to circuit C1, supply voltage V2 is applied to circuit C2 and C3, and so forth.

The tailoring of the supply voltages V1–Vn to the particular circuits C1–Cn is dependent upon the frequency at which the circuits C1–Cn are required to be operated. For example, and as previously described, the logic delay of such CMOS circuits C1–Cn increases drastically as the supply voltage is reduced to near 1 volt. If such logic delay is tolerable, the supply voltage provided to a particular circuit will drastically reduce the power consumption for that particular circuit as the energy is reduced in proportion to the square of the supply voltage ($V_{DD}$). f such logic delay is not tolerable, however, because by way of example the logic circuit performs a function that must be completed within a particular period of time, the reduction of the supply voltage ($V_{DD}$) applied to such a circuit will be limited depending upon the acceptable logic delay. The supply voltage $V_{DD}$ for any particular circuit may be reduced as low as possible, however, and yet meet speed requirements.

Integrated circuit 102 may include various circuits C1–Cn like those described in reference to FIG. 3. Supply voltage source 106 may be implemented using a variety of components and may include any number of voltage sources wherein each provides a single supply voltage level. Supply voltage 106 may also include one or more adjustable voltage sources for providing supply voltage levels over a continuous range of levels. Supply voltage 106 may further include a voltage source that is operable to provide discrete supply voltage levels (as opposed to levels which vary over a continuous range). The supply voltage source may include a voltage divider, a voltage regulator, a charge pump, or any other elements that provide supply voltage, V1–Vn. It is generally preferred that supply voltage source 106 be configured as a charge pump.

Supply voltage ($V_{DD}$) is generally in the range of about 3 volts to about 6 volts. It is preferred that supply voltages V1–Vn range between about 1 volt to about 3 volts, depending on the particular CMOS, CML, SOS, SOI, BICMOS, PMOS and/or NMOS circuitry or technology employed.

With reduction in supply voltage ($V_{DD}$), threshold voltage ($V_T$) for the circuits,, is also reduced. With supply voltages ranging between about 3 volts and about 6 volts, for example, the threshold voltage for CMOS, CML, SOS, SOI, BICMOS, PMOS and/or NMOS devices is generally in the range of about 0.8 volts to about 1.0 volt. In implantable medical devices, it is generally preferred that lithium chemistries be utilized for implantable batteries. Such lithium chemistries are generally characterized in having open or closed circuit voltages that range between about 2.8 volts and about 3.3 volts. CMOS, CML, SOS, SOI, BICMOS, PMOS and/or NMOS circuitry generally has an associated threshold voltage of about 0.75. By reducing supply voltages below 2.8 volts, voltage thresholds for CMOS CML, SOS, SOI, BICMOS and/or NMOS devices may be decreased to as low as about 0.2 volts or 0.3 volts.

Currently, various ultra low power logic designs operate at supply voltages as low as about 1.1 volts. Logic designs for microprocessors for laptop and other portable product designs often utilize such low voltages. By utilizing the tailored supply voltages V1–Vn, low power or ultra low power logic designs may be used for at least some of the various circuits C1–Cn of integrated circuit 102. Other circuits may require supply voltages of a higher nature. With use of lower threshold levels due to lower supply voltages, static power consumption losses undesirably increase by several orders of magnitude.

Multiple supply voltage system 100 may therefore further include optional back gate bias source 130 for providing back gate bias voltages BV1–BVn to circuits C1–Cn of integrated circuit 102. Generally, back gate bias voltages BV1–BVn depend on supply voltage V1–Vn applied to circuits C1–Cn to adjust the threshold voltages for devices of circuits C1–Cn. Threshold voltage ($V_T$) for CMOS, CML, SOS, SOI, BICMOS, PMOS and/or NMOS devices of the circuit, for example, may be set at a lower voltage by providing a back gate bias voltage to the particular circuits supplied with the lower supply voltage. Moreover, if circuit C1 is supplied with a lower supply voltage V1, then back gate bias voltage BV1 may optionally be applied to circuit C1 to adjust the threshold voltage ($V_T$) for CMOS, CML, SOS, SOI, BICMOS, PMOS and/or NMOS devices to a higher threshold voltage ($V_T$) value. In this manner, static leakage current losses may be minimized because the equivalent higher threshold voltage has been restored. Additionally, a broader range of supply voltages is possible because the back gate adjustment allows a tailoring of the threshold to permit high/low speed operation and eliminating the static current drain leakage.

The back gate bias voltage may be provided by, for example, a fixed voltage source (e.g., a charge pump) connected to the back gate well via a contact. Alternatively, an active body bias scheme wherein the voltage source is selectable or adjustable over an appropriate range may be employed.

Back gate voltages may be applied in any known manner. For example, the application of back gate bias voltages is described in various patent references including U.S. Pat. No. 4,791,318 to Lewis et al., U.S. Pat. No. 4,460,835 to Masuoka, U.S. Pat. No. 5,610,083 to Chan et al., and U.S. Pat. No. 5,185,535 to Farb et al., all incorporated by reference herein in their respective entireties.

Figure 6:
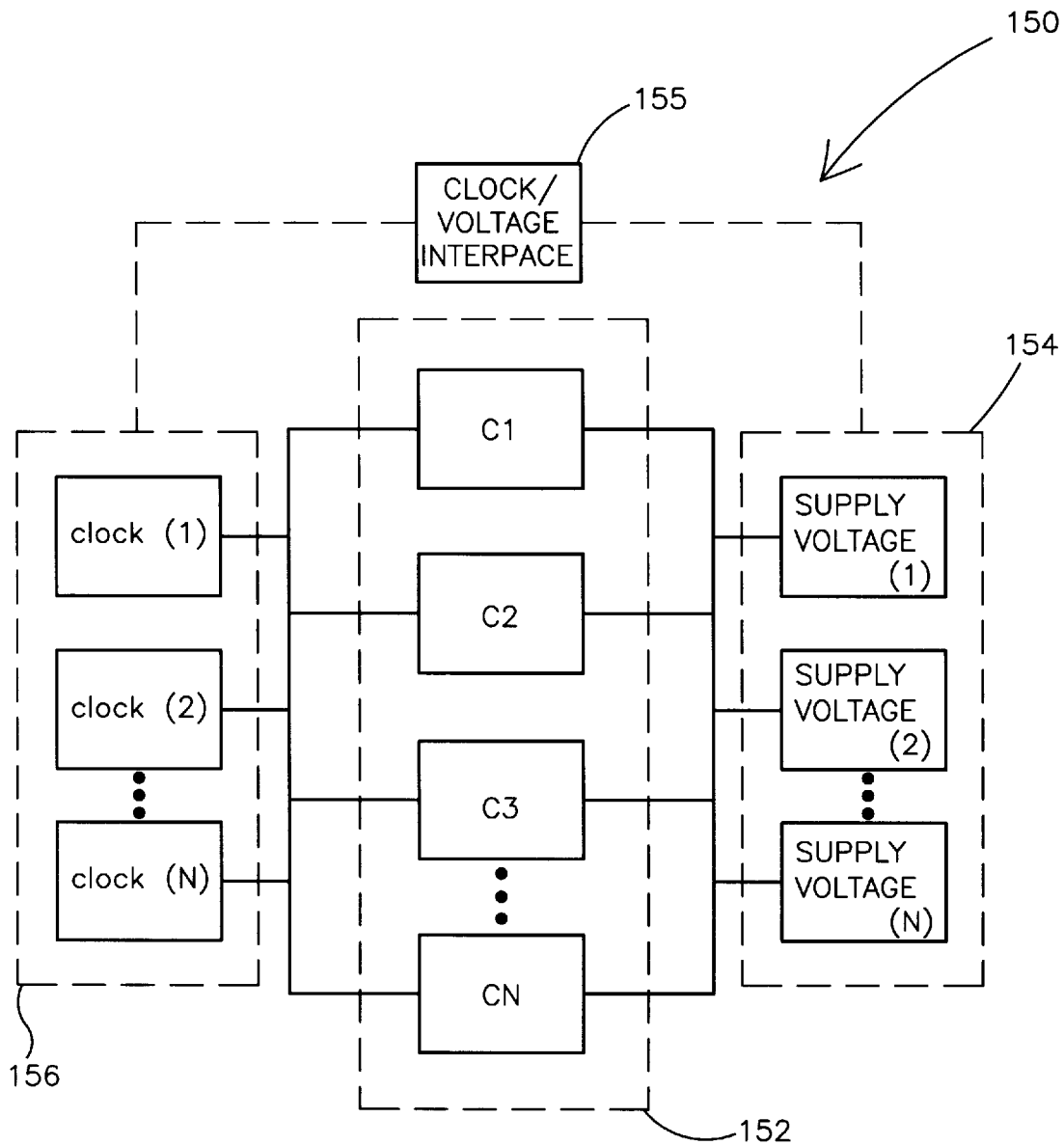
FIG. 6 is a block diagram illustrating a variable supply voltage system according to the present invention.

FIG. 6 shows a general block diagram of a variable supply voltage/variable clock system 150 according to the present invention. System 150 includes integrated circuit 152, clock source 156, supply voltage source 154, and clock/supply voltage interface 155. Supply voltage source 154 is operable for providing a plurality of supply voltages V1–Vn to a plurality of circuits C1–Cn of integrated circuit 152. Clock source 156 of system 150 is operable for providing clock signals at a plurality of frequencies, clock1–clockn. Circuits C1–Cn are similar to those described in reference to FIG. 3. Clock source 156 is similar to clock source 34 described in reference to FIG. 3. Supply voltage source 154 is similar to supply voltage source 106 described in reference to FIG. 5. In variable supply voltage/variable clock system 150, however, clock/voltage interface 155 is used to adjust supply voltages V1–Vn applied to circuits C1–Cn "on the fly" as required by the specific timing functions of circuits C1–Cn.

In an illustrative example, circuit C1 may be a particular logic circuit for performing one or more particular functions. Such functions, however, may be required to be performed in a first time period at a first clock frequency and during a different second time period at a second clock frequency to perform such function within the allowed time of the respective first and second time periods. In other words, one time period is shorter than the other and, as such, those functions which require performance over a certain number of cycles must be performed at a higher clock frequency if they are to be completed within a time period that is shorter than another time period.

In such an example, and according to the present invention, clock/voltage interface 155 detects the clock signal applied to circuit C1 during the first time period in which the higher frequency clock signal is used and accordingly provides supply voltage source 154 with a signal to select and apply a certain supply voltage corresponding to the higher clock frequency. Thereafter, when the lower clock frequency is applied to circuit C1 during the second time period, clock/voltage interface 155 senses the use of the lower clock frequency and applies a signal to voltage supply source 154 for application of a certain supply voltage corresponding to the lower clock frequency for application to circuit C1.

Additionally, circuit C2 may be a CMOS, CML, SOS, SOI, BICMOS, PMOS and/or NMOS processor which may also have clock frequency and corresponding supply voltage adjustments made "on the fly." Such a system will become readily apparent to those skilled in the art following the below discussion referring to FIG. 7.

Figure 7:
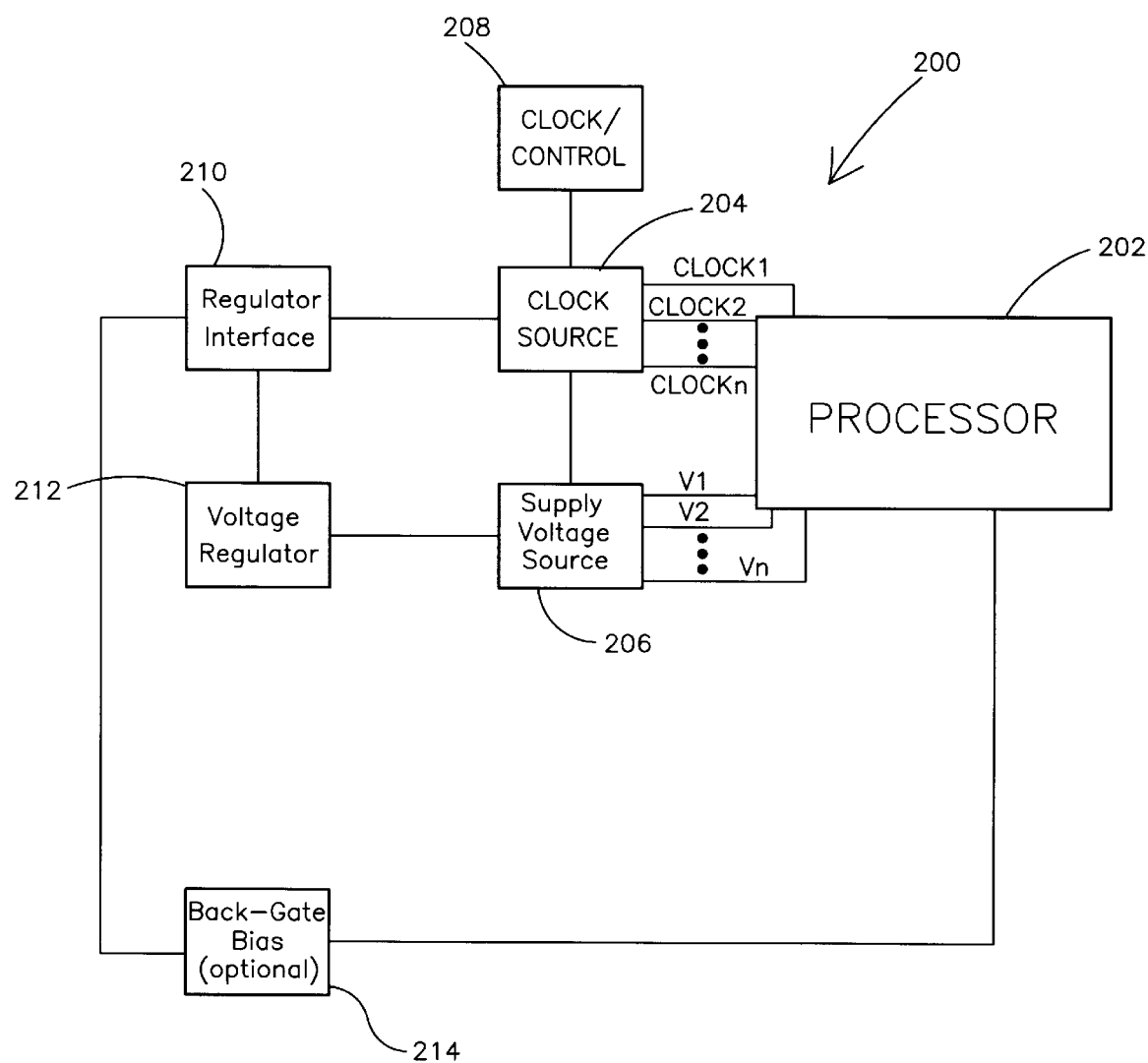
FIG. 7 is a block diagram of clock controlled processing circuitry according to the present invention.

FIG. 7 shows a general block diagram of a clock controlled processing system 200 according to the present invention. The clock controlled processing system 200 includes processor 202 (e.g., a CMOS, CML, SOS, SOI, BICMOS, PMOS and/or NMOS microprocessor or CMOS, CML, SOS, SOI, BICMOS, PMOS and/or NMOS digital signal processor), clock source 204, supply voltage source 206, voltage regulator 212, regulator interface 210, clock control 208, and optional back gate bias source 214. In a manner similar to that described in reference to FIG. 6, supply voltage 206 applied to processor 202 is changed "on the fly" as required by specific circuit timing requirements.

Generally, processor 202 is operated under control of clock source 204. Depending upon the processing capability required, clock source 204 may operate processor 202 at any one of a plurality of clock frequencies. Such clock frequencies will be selected under the control of clock control 208. Clock control 208 may be part of any timing and control hardware and/or timing and control software used to control operation of processor 202 as part of a larger system. For example, such clock control may take the form of a digital controller/timer circuit for performing timing control of an implantable medical device.

Processor 202 may perform any number of functions as appropriate for the device in which it is used. High frequency processing capabilities (i.e., about 250 KHz to about 10 MHz), low frequency processing capabilities (i.e., about 1 Hz to about 32 KHz), and processing capabilities with regard to frequencies between such limits are contemplated according to the present invention. For simplicity purposes, clock control processing system 200 operation is described in reference to processor 202 performing only two different functions, each during a predetermined respective period of time. For example, with respect to an implantable medical device such as a pacemaker, during the first period of time, a high processing function requiring a relatively high clock frequency may include a function such as telemetry uplink/downlink, morphology detection, initialization, arrhythmia detection, far-field R-wave detection, EMI detection, retrograde conduction, etc. On the other hand, low frequency processing functions may include a function such as sensing intrinsic beats, pacing, low speed telemetry, transtelephonic data transfer, remote monitoring, battery checks, etc.

When processor 202 performs high frequency processing functions during a predetermined time period, a relatively high clock frequency (e.g., 250 KHz to 10 MHz) may be supplied by clock source 204 for operation of processor 202. Regulator interface 210 will detect the higher clock frequency applied to processor 202 for operation during the high processing function and apply a control signal to voltage regulator 212 for regulation of the supply voltage source 206. Supply voltage source 206 is operable under control of voltage regulator is 212 to provide a supply voltage within a predetermined range, preferably between about 1.1 volts and about 3 volts. When a high clock frequency is used for operation of processor 202 for high frequency processing functions, supply voltage source 206 generally applies a supply voltage in the upper range of the preferred supply voltages to the CMOS devices of processor 202.

On the other hand, when processor 202 is to execute low frequency processing functions during the predetermined periods of time, clock control 208 signals clock source 204 to apply a lower frequency for operation of processor 202. As such, regulator interface 210 detects the lower frequency being used to operate processor 202 and issues a control signal to voltage regulator 212 for regulation of supply voltage source 206 such that a lower supply voltage in the lowered of the preferred range of supply voltages is applied to the CMOS, CML, SOS, SOI, BICMOS, PMOS and/or NMOS devices of processor 202.

It will be recognized by one skilled in the art that any intermediate processing capability may be achieved between the higher frequency and the lower frequency capabilities described above and that the present invention is in no manner limited to processing at only two clock frequencies and at two corresponding supply voltages. Rather, multiple levels of processing capability can be achieved according to the present invention with associated clock frequencies and corresponding supply voltages being applied to processor 202.

FIG. 4C illustrates one embodiment of the clock control processing system 200. As shown therein, during the overall cardiac cycle of predetermined time period x, a high frequency is used for controlling operation of processor 202 during time period 71 of the cardiac cycle time period x, e.g., during processing of the QRS complex. Thereafter, a lower clock frequency is used during time period y for controlling operation of processor 202 to perform any of a number of other different functions, such as cardiac event/EMI differentiation functions. During operation of processor 202 at the higher clock frequency during time period 71, a higher supply voltage from supply voltage source 206 is applied to the CMOS, CML, SOS, SOI, BICMOS, PMOS and/or NMOS devices of processor 202. Likewise, during operation of the processor 202 at the relatively lower clock frequency, a lower supply voltage from supply voltage source 206 is applied to the CMOS, CML, SOS, SOI, BICMOS, PMOS and/or NMOS devices of processor 202 during time period y of the overall cardiac cycle time period x.

Furthermore, and as shown in FIG. 7, an optional back gate bias 214 may be used to dynamically adjust the threshold voltage ($V_T$) of CMOS, CML, SOS, SOI, BICMOS, PMOS and/or NMOS devices of processor 202 as a function of the clock frequency applied to processor 202 by clock source 204. The regulator interface 210 detects the clock frequency used to control operation of processor 202 and controls the voltage level of back gate bias 214 to be applied to the CMOS, CML, SOS, SOI, BICMOS, PMOS and/or NMOS devices of processor 202. The dynamic adjustment of the threshold voltage may be implemented as an adjustable or selectable voltage source utilizing, for example, a charge pump and a regulator. The back gate voltage and the "normal" gate voltage provide a gate bias or voltage to the transistor. By adjusting the back gate voltage, the "apparent" voltage is increased with a resultant reduction in leakage current.

Figure 8:
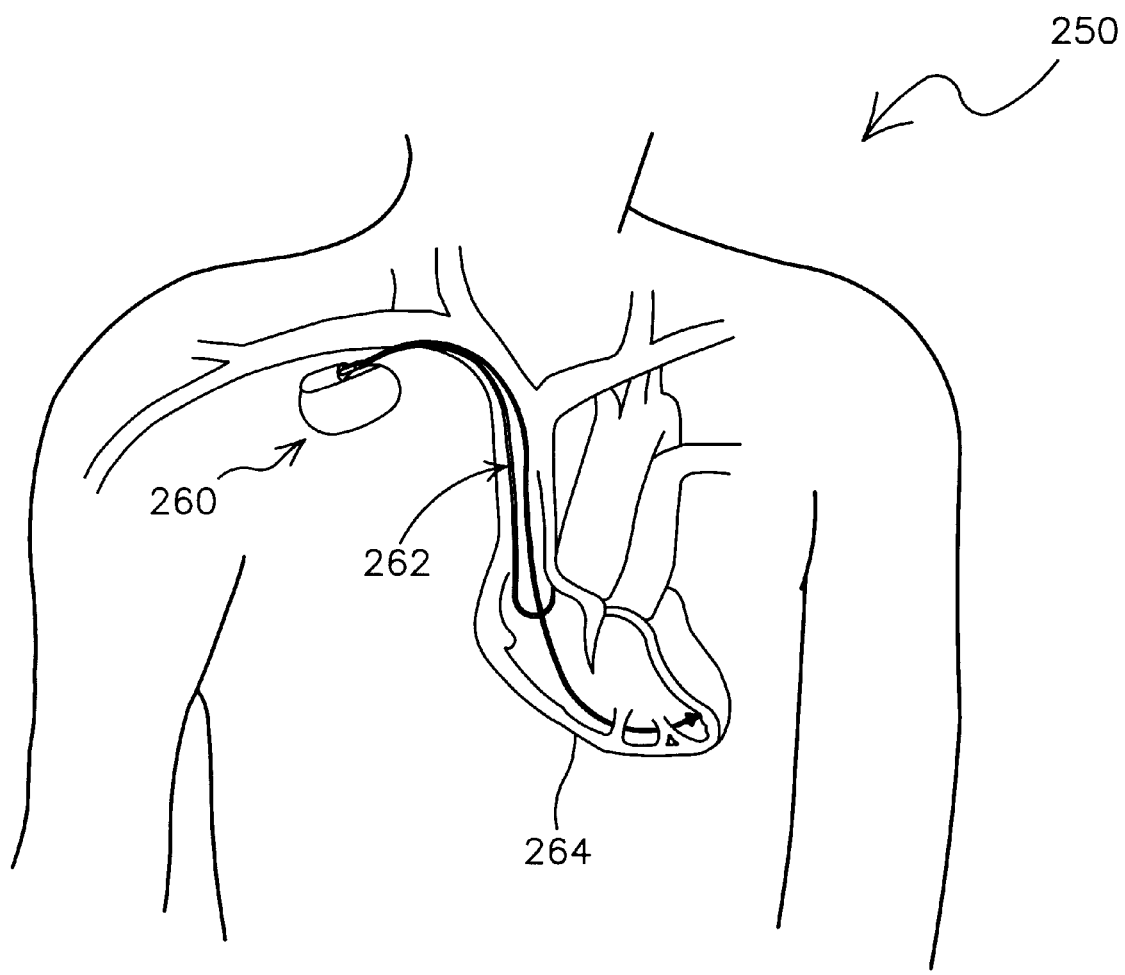
FIG. 8 is a diagram illustrating an implantable medical device in a body.

FIG. 8 is a simplified diagram of an implantable medical device 260 for which the present invention is useful. The implantable device 260 is implanted in body 250 near mammalian heart 264. Implantable medical device 260 is connected to heart 264 by leads 262. In the case where the device 260 is a pacemaker, leads 262 are pacing and sensing leads to sense electrical signals attendant to the depolarization and repolarization of heart 264 and provide pacing pulses in the vicinity of the distal ends thereof. Implantable medical device 260 may be any implantable cardiac pacemaker such as those disclosed in U.S. Pat. No. 5,158,078 to Bennett et al., U.S. Pat. No. 5,387,228 to Shelton, U.S. Pat. No. 5,312,453 to Shelton et al., or U.S. Pat. No. 5,144,949 to Olson, all hereby incorporated herein by reference in their respective entireties, and all of which may be modified advantageously in accordance with the present invention.

Figure 10:
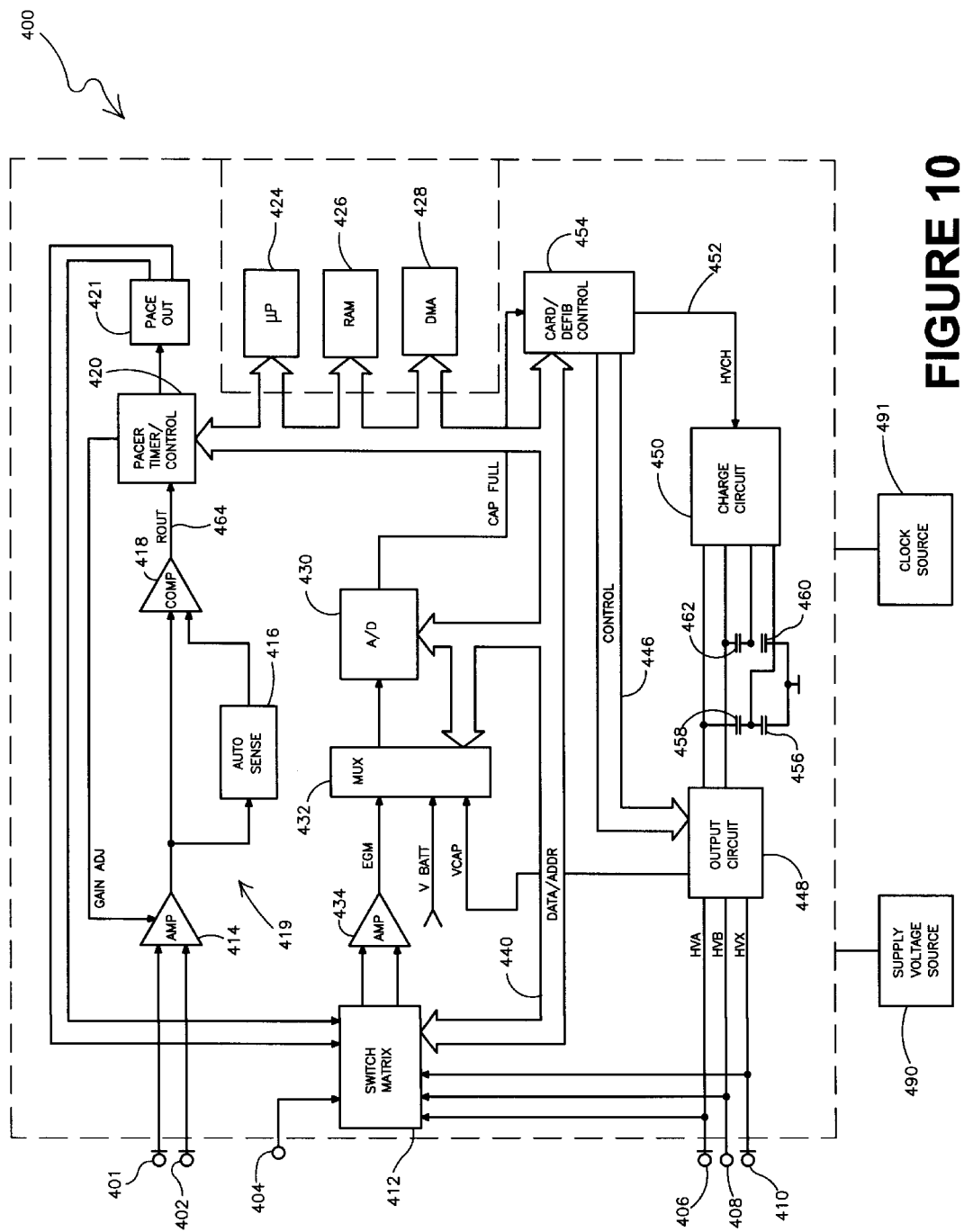
FIG. 10 is a schematic block diagram of an implantable pacemaker/cardioverter/defibrillator (PCD) for use in illustrating one or more embodiments of the present invention.

Implantable medical device 260 may also be a pacemaker/cardioverter/defibrillator (PCD) corresponding to any of the various commercially-available implantable PCDs, one of which is summarily described herein with reference to FIG. 10 and described in detail in U.S. Pat. No. 5,447,519. In addition to the PCD described in U.S. Pat. No. 5,447,519, the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,,388 to Pless, or U.S. Pat. No. 4,821,723 to Baker et al., all hereby incorporated herein by reference in their respective entireties. Those devices may be employed using the present invention in that such devices may employ or be modified with circuitry and/or systems according to the present invention.

Alternatively, implantable medical device 260 may be an implantable nerve stimulator or muscle stimulator such as those disclosed in U.S. Pat. No. 5,199,428 to Obel et al., U.S. Pat. No. 5,207,218 to Carpenter et al., or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of electrical device which uses CMOS circuit design and is believed to be particularly advantageous where low power is desired, particularly in implantable medical devices.

Finally, implantable medical device 260 may be a cardioverter, an implantable pulse generator (IPG) or an implantable cardioverter-defibrillator (ICD).

It is to be understood, however, that the scope of the present invention is not limited to implantable medical devices or medical devices only, but includes any type of electrical device which employs CMOS, CML (Current Mode Logic), SOS (Silicon on Sapphire), SOI (Silicon on Insulator), BICMOS, PMOS and/or NMOS circuitry or circuit design where low power consumption is desired.

In general, implantable medical device 260 includes an hermetically-sealed enclosure that includes an electrochemical cell such as a lithium battery, CMOS, CML, SOS, SOI, BICMOS, PMOS and/or NMOS circuitry that controls device operations, and a telemetry transceiver antenna and circuit that receives downlinked telemetry commands from and transmits stored data in a telemetry uplink to an external programmer. The circuitry may be implemented in discrete logic and/or may include a microcomputer-based system with A/D conversion.

It is to be understood that the present invention is not limited in scope to particular electronic features and operations of particular implantable medical devices and that the present invention may be useful in conjunction with various implantable devices. Further, the present invention is not limited in scope to implantable medical devices including only a single processor but may be applicable to multiple-processor devices as well.

Figure 9:
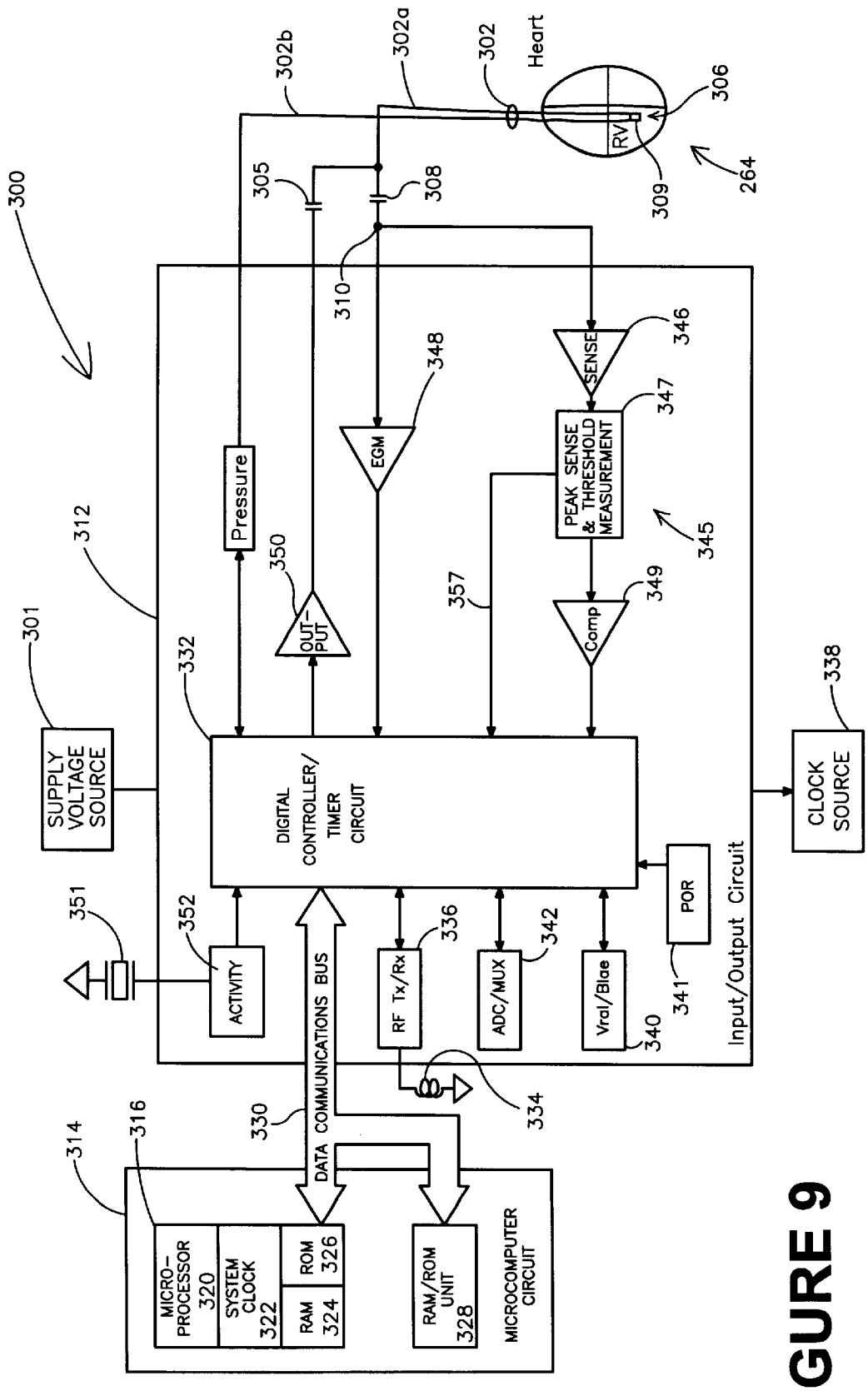
FIG. 9 is a block diagram of the circuitry of a pacemaker for use in illustrating one or more embodiments of the present invention.

FIG. 9 shows a block diagram illustrating the components of pacemaker 300 in accordance with one embodiment of the present invention. Pacemaker 300 has a microprocessor-based architecture. However, illustrative pacemaker 300 of FIG. 9 is only one exemplary embodiment of such devices and it will be understood that it could be implemented in any logic-based, custom integrated circuit architecture, if desired, as can any microprocessor-based system.

In the illustrative embodiment shown in FIG. 9, pacemaker 300 is most preferably programmable by means of an external programming unit (not shown in the figures). One such programmer suitable for the purposes of the present invention is the commercially available Medtronic Model 9790 programmer. The programmer is a microprocessor-based device which provides a series of encoded signals to pacemaker device 300 by means of a programming head which transmits radio frequency (RF) encoded signals to antenna 334 of pacemaker 300 according to a telemetry system such as, for example, that described in U.S. Pat. No. 5,127,404 to Wyborny et al., the disclosure of which is hereby incorporated by reference herein in its entirety. It is to be understood, however, that any programming methodology may be employed so long as the desired information is transmitted to and from the pacemaker.

Pacemaker 300 illustratively shown in FIG. 9 is electrically coupled to the patient's heart 264 by leads 302. Lead 302a including electrode 306 is coupled to a node 310 in the circuitry of pacemaker device 300 through input capacitor 308. Lead 302b is coupled to pressure circuitry 354 of input/output circuit 312 to provide a pressure signal from sensor 309 to the circuit 354. The pressure signal is used to ascertain metabolic requirements and/or cardiac output of a patient. Further, activity sensor 351, such as a piezoceramic accelerometer, provides a sensor output to activity circuit 352 of input/output circuit 312. The sensor output varies as a function of a measured parameter that relates to metabolic requirements of a patient. Input/output circuit 312 contains circuits for interfacing to heart 264, to activity sensor 351, to antenna 334, to pressure sensor 309 and circuits for application of stimulating pulses to heart 234 to control its rate as a function thereof under control of software-implemented algorithms in microcomputer unit 314.

Microcomputer unit 314 preferably comprises on-board circuit 316 that include, microprocessor 320, system clock circuit 322, and on-board random access memory (RAM) 324 and read only memory (ROM) 326. In this illustrative embodiment, off-board circuit 328 comprises a RAM/ROM unit. On-board circuit 316 and off-board circuit 328 are each coupled by a communication bus 330 to digital controller/timer circuit 332.

According to the present invention, the circuits shown in FIG. 9 are powered by an appropriate implantable battery supply voltage source 301 (e.g., a voltage source generally shown in FIGS. 1–7). For the sake of clarity, the coupling of supply voltage source 301 to various circuits of pacemaker 300 is not shown in the figures. Further, the circuits operable under control of a clock signal shown in FIG. 9 are operated according to the present invention under clock source 338. For the sake of clarity, the coupling of such clock signals from the clock, source 338 (e.g., a clock source generally shown in FIGS. 1–7) to such CMOS, CML, SOS, SOI, BICMOS, PMOS and/or NMOS circuits of pacemaker 300 is not shown in the Figures.

Antenna 334 is connected to input/output circuit 312 to permit uplink/downlink telemetry through RF transmitter and receiver unit 336. Unit 336 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

$V_{REF}$ and bias circuit 340 generates a stable voltage reference and bias currents for circuits of input/output circuit 312. Analog-to-digital converter (ADC) and multiplexer unit 342 digitize analog signals and voltages to provide "real-time" telemetry intracardiac signals and battery end-of-life (EOL) replacement function. A power on reset circuit 341 functions as a means to reset circuitry.

Operating commands for controlling the timing of pacemaker device 300 are coupled by bus 330 to digital controller/timer circuit 332, where digital timers and counters establish the overall escape interval of the pacemaker device 300 as well as various refractory, blanking, and other timing windows for controlling the operation of the peripheral components disposed within input/output circuit 312.

Digital controller/timer circuit 332 is preferably coupled to sense circuitry 345 and to electrogram (EGM) amplifier 348 for receiving amplified and processed signals sensed by electrode 306 disposed on lead 302a. Such signals are representative of the electrical activity of the patient's heart 264. Sense amplifier 346 of circuitry 345 amplifies sensed electrocardiac signals and provides an amplified signal to peak sense and threshold measurement circuitry 347. Circuit 347 in turn provides an indication of peak sensed voltages and measured sense amplifier threshold voltages on path 357 to digital controller/timer circuit 332. An amplified sense amplifier signal is also provided to comparator/threshold detector 349. The sense amplifier may correspond to that disclosed in U.S. Pat. No. 4,379,459 to Stein, which is hereby incorporated by reference herein in its entirety.

The electrogram signal provided by EGM amplifier 348 is employed when pacemaker 300 is being interrogated by an external programmer (not shown) to transmit by uplink telemetry a representation of an analog electrogram of the patient's electrical heart activity. Such functionality is, for example, shown in U.S. Pat. No. 4,556,063 to Thompson et al., previously incorporated by reference.

Output pulse generator and amplifier 350 provides pacing stimuli to patient's heart 264 through coupling capacitor 305 and electrode 306 in response to a pacing trigger signal provided by digital controller/timer circuit 332. Output amplifier 350 may correspond generally to the output amplifier disclosed in U.S. Pat. No. 4,476,868 to Thompson, also incorporated by reference herein in its entirety. The circuits of FIG. 9 which may be any one of CMOS, CML, SOS, SOI, BICMOS, PMOS and/or NMOS circuitry capable of operation according to the present invention include processor 320, digital controller timer circuit 332, RAM 324, ROM 326, RAM/ROM unit 328 and ADC/Mux 342.

FIG. 10 is a functional schematic diagram from U.S. Pat. No. 5,447,519 to Peterson, which shows implantable PCD 400 in which the present invention may usefully be practiced. This diagram is an illustration to be taken only as an exemplary type of device in which the invention may be embodied, and not as limiting to the scope of the present invention. Other implantable medical devices as previously described having functional organizations wherein the present invention may be useful may also be modified in accordance with the present invention. For example, the present invention is also believed to be useful in conjunction with implantable PCDs as disclosed in prior U.S. Pat. No. 4,548,209 to Wielders et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their entireties.

Illustrative PCD 400 is provided with six electrodes 401, 402, 404, 406, 408, and 410. For example, electrodes 401 and 402 may be a pair of closely-spaced electrodes positioned in the ventricle of the heart 264. Electrode 404 may correspond to a remote, indifferent electrode located on the housing of the implantable PCD 400. Electrodes 406, 408, and 410 may correspond to large surface area defibrillation electrodes located on leads to the heart 264 or epicardial electrodes.

Electrodes 401 and 402 are shown as hard-wired to the near field (i.e., narrowly spaced electrodes) R-wave detector circuit 419 comprising band pass filtered amplifier 414, auto threshold circuit 416 (for providing an adjustable sensing threshold as a function of the measured R-wave amplitude), and comparator 418. An Rout signal 464 is generated whenever the signal sensed between electrodes 401 and 402 exceeds a sensing threshold defined by auto threshold circuit 416. Further, the gain on amplifier 414 is adjusted by pacer timer and control circuitry 420. The sense signal, for example, is used to set the timing windows and to align successive waveshape data for morphology detection purposes. For example, the sense event signal 464 may be routed through the pacer/timer control circuit 420 on bus 440 to processor 424 and may act as an interrupt for the processor 424 such that a particular routine of operations, e.g., morphology detection, discrimination functions, is commenced by processor 424.

Switch matrix 412 is used to select available electrodes under control of processor 424 via data/address bus 440 such that the selection includes two electrodes employed as a far field electrode pair (i.e., widely spaced electrodes) in conjunction with a tachycardia/fibrillation discrimination function (e.g., a function to discriminate between tachycardia, i.e., an abnormally fast heart rate, and fibrillation, i.e., uncoordinated and irregular heartbeats, so as to apply an appropriate therapy). Far field EGM signals from the selected electrodes are passed through band pass amplifier 434 and into multiplexer 432, where they are converted to digital data signals by analog to digital converter (ADC) 430 for storage in random access memory 426 under control of direct memory access circuit 428. For example, a series of EGM complexes for several seconds may be performed.

According to the present invention, the circuits shown in FIG. 10 are powered by an appropriate implantable battery supply voltage source 490 (e.g., a voltage source generally shown in FIGS. 1–7). For the sake of clarity, the coupling of supply voltage source 490 to various circuits of PCD 400 is not shown in the Figures. Further, the circuits operable under control of a clock signal shown in FIG. 10 are operated according to the present invention under clock source 491. For the sake of clarity, the coupling of such clock signals from the clock source 491 (e.g., a clock source generally shown in FIGS. 1–7) to such CMOS, CML, SOS, SOI, BICMOS, PMOS and/or NMOS circuits of PCD 400 is not shown in the Figures.

The occurrence of an R-wave sense event or detect signal Rout 464 is communicated to processor 424 to initiate morphology analysis on waveforms by processor 424 for use in selection of a therapy for heart 264. For example, the processor may calculate the cumulative beat-to-beat variability of heart 264, time intervals separating R-wave sense events, and various other functions as set out in numerous references including any of the references already listed herein and various other references with regard to implantable PCDs.

Other portions of PCD 400 of FIG. 10 are dedicated to the provision of cardiac pacing, cardioversion, and defibrillation therapies. With regard to cardiac pacing, the pacer timing/control circuit 420 includes programmable digital counters which control the basic timing intervals associated with cardiac pacing, including the pacing escape intervals, the refractory periods during which sensed R-waves are ineffective to restart timing of escape intervals, etc. The durations of such intervals are typically determined by processor 424 and communicated to pacer timer/control circuit 420 via address/data bus 440. Further under control of processor 424, pacer timing/control circuit also determines the amplitude of such cardiac pacing pulses and pace out circuit 421 provides such pulses to the heart.

In the event that a tachyarrhythmia (i.e., tachycardia) is detected, and an anti-tachyarrhythmia pacing therapy is desired, appropriate timing intervals for controlling generation of anti-tachycardia pacing therapies are loaded from processor 424 into pacer timing and control circuitry 420. Similarly, in the event that generation of a cardioversion or defibrillation pulse is required, processor 424 employs the counters and timing and control circuitry 420 to control timing of such cardioversion and defibrillation pulses.

In response to detection of fibrillation or a tachycardia requiring a cardioversion pulse, processor 424 activates cardioversion/defibrillation control circuitry 454, which initiates charging of the high voltage capacitors 456, 458, 460 and 462 via charging circuit 450 under control of high voltage charging line 452. Thereafter, delivery of the timing of the defibrillation or cardioversion pulse is controlled by pacer timing/control circuitry 420. Various embodiments of an appropriate system for delivering and synchronization of cardioversion and defibrillation pulses, and controlling the timing functions related to them is disclosed in more detail in U.S. Pat. No. 5,188,105 to Keimel, which is incorporated herein by reference in its entirety. Other such circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,375,817 to Engle et al., all incorporated herein by reference in their entireties. Further, known circuitry for controlling the timing and generation of anti-tachycardia pacing pulses is described in U.S. Pat. No. 4,577,633 to Berkovits et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their entireties.

Selection of a particular electrode configuration for delivery of the cardioversion or defibrillation pulses is controlled via output circuit 448 under control of cardioversion/defibrillation control circuit 454 via control bus 446. Output circuit 448 determines which of the high voltage electrodes 406, 408 and 410 will be employed in delivering the defibrillation or cardioversion pulse regimen.

The components of PCD 400 of FIG. 10 which are CMOS, CML, SOS, SOI, BICMOS, PMOS and/or NMOS circuitry capable of operation according to the present invention include processor 424, control circuits 420 and 454, RAM 426, DMA 428, ADC 430, and multiplexer 432.

According to the present invention, pacemaker 300 illustrated in FIG. 9 and PCD 400 illustrated in FIG. 10 may both be implemented in accordance with the generalized embodiments previously described herein with reference to FIGS. 1–7. First, for example, with respect to pacemaker 300 of FIG. 9, voltage supply source 301 of pacemaker 300 may be implemented in a manner previously described with reference to FIGS. 1–7. Likewise, clock source 338 of pacemaker 300 may be implemented in such a manner as described with reference to FIGS. 1–7. Similarly, clock source 491 of PCD 400 of FIG. 10 and voltage supply source 490 of PCD 400 of FIG. 10 may be implemented in accordance with the generalized embodiments previously described herein with reference to FIGS. 1–7.

As one illustrative example, ADC/Mux 342, RF transmitter/receiver 336, digital controller timer circuit 332, and various other CMOS, CML, SOS, SOI, BICMOS, PMOS and/or NMOS circuits may be individually operated at different clock frequencies available from clock source 338. Likewise, such circuits may be operated at corresponding supply voltages which may be different for each of the circuits. Moreover, RF transmitter/receiver 336 may be operated during a particular time period (e.g., when uplinking) at a particular clock frequency available from clock source 338 and at a particular supply voltage available from voltage supply source 301 corresponding to the particular clock frequency. On the other hand, during a different time period (e.g., during downlink), circuit 336 may be operated at a completely different clock frequency and supply voltage.

Automatic adjustment of telemetry parameters under certain circumstances is described in U.S. Pat. No. 5,683,432 to Goedeke et al.

Additionally, and in respect of FIG. 10, AND converter circuit 430, cardioverter/defibrillator control circuit 454, and various other circuits such as RAM 426, DMA 428, and multiplexer 432 may also be operated at different clock frequencies available from clock source 491 and at different corresponding supply voltages available from supply voltage source 490. Further, a telemetry circuit (not shown in the Figures) may be employed with PCD 400 of FIG. 10 and may also be operated at different clock frequencies available from clock source 491 and at different corresponding supply voltages available from supply voltage source 490. Processor 424 may also be operated at different clock speeds depending on the function being performed by processor 424 (such as that described in reference to FIG. 7). Morphology detection sensing at typical physiologic rates (i.e., 50 to 150 BPM), for example, may be performed at a first clock frequency and corresponding supply voltage while arrhythmia detection may be performed at a different clock frequency and corresponding supply voltage.

Figure 11:
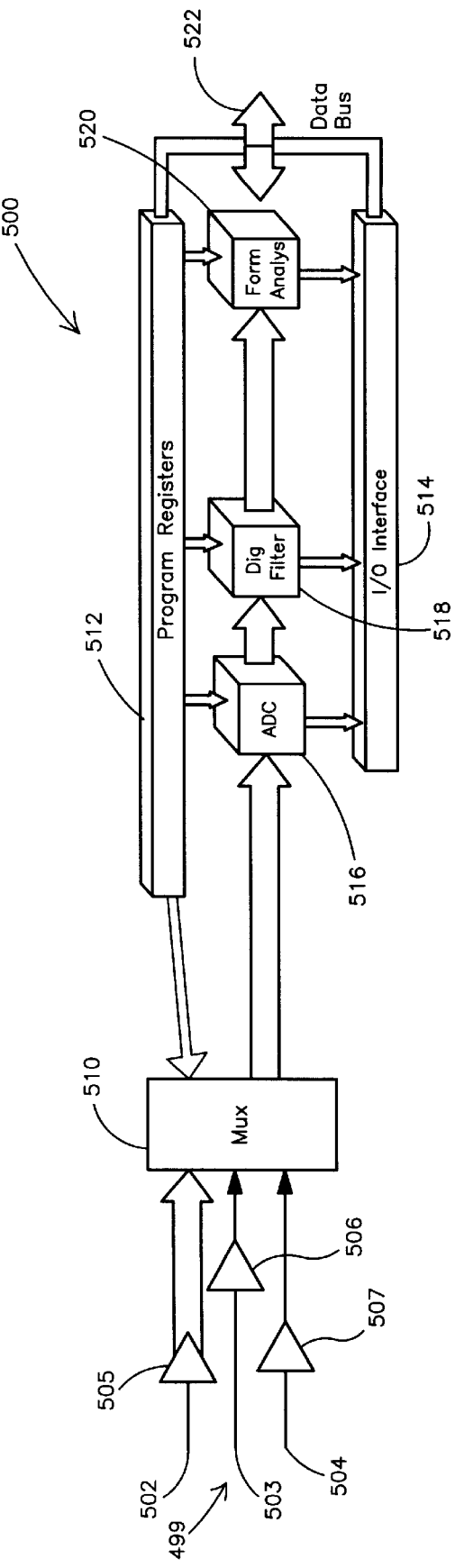
FIG. 11 is a schematic block diagram illustrating a variable clock/variable supply voltage digital signal processing system according to the presents invention.

FIG. 11 shows a variable clock/variable supply voltage digital signal processing (DSP) system 500 which may be used in conjunction with and/or in the alternative to certain circuits shown in FIGS. 9 and 10. DSP system 500 according to FIG. 11 may be used, for example, in place of activity circuit 352, pressure circuit 354, sense amplifier circuit 346 (for P-wave, R-wave and/or T-wave sense amplifiers), and further may be provided with additional functionality with use of a pseudo EKG signal 502. Generally, any number of analog signals 499, for, example, such as pseudo EKG signals 502, activity sensor signal 503 and pressure and onset sensor signal 504, may be provided through respective to amplifiers 505–507. Amplified signals are then presented to multiplexer 510, which in turn provides them to analog to digital converter (ADC) 516 in cycled fashion Signals 502–504 may be cycled at different rates by cycling through the outputs of the several amplifiers/preamplifiers 505–507 such as those described in pending U.S. patent application Ser. No. 08/801,335, Medtronic Docket No. P-4521, entitled "Method for Compressing Digitized Cardiac Signals Combining Lossless Compression and Non-linear Sampling" (which describes variable compression ADC sampling, and which is hereby incorporated herein by reference in its entirety). The ADC may also have variable conversion rates such as those described in U.S. Pat. No. 5,263,486 and U.S. Pat. No. 5,312,416 (which are also hereby incorporated herein by reference in their respective entireties).

Input/output interface 514 and program registers 512 are utilized under control of a timing circuit (not shown in the Figures) to control application of analog signals from multiplexer 510 to ADC 516, which in turn provides such converted digital signals to digital filter 518 to provide a signal to waveform analysis processor 520 (i.e., a digital signal processor (DSP)). To reduce power, waveform analysis processor 520 may be clocked at different speeds or controlled "on the fly" in accordance with at least one embodiment of the present invention, depending on the particular processing needs at hand. Only during a QRS complex, for example, does waveform analysis processor 520 operate in a high speed processing mode at a relatively high frequency. Conversely, for example, during the remainder of the cardiac cycle processor 520 may be "idling along" at a much lower clock frequency. Such a processing cycle has been previously described in reference to FIG. 4C.

In addition to the lower clock speed utilized for different portions of the cardiac cycle, one skilled in the art will now recognize that in accordance with the other aspects of the present invention, as processor speed is reduced, supply voltage level ($V_{DD}$) may also be reduced accordingly. Thus, reduced power consumption is attained as previously described.

Figure 12:
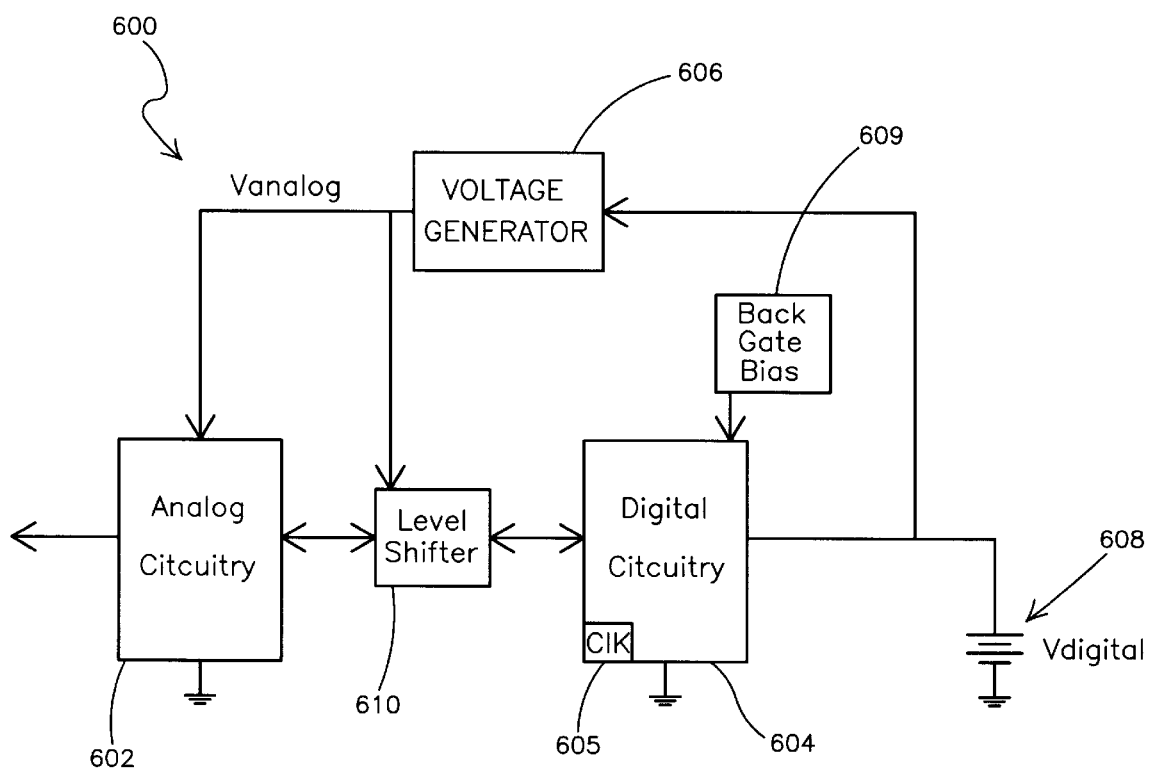
FIG. 12 is a general schematic block diagram of a device according to the present invention using different supply voltages for analog and digital circuits of the device.

FIG. 12 is a general schematic block diagram of device 600 including analog circuitry 602 and digital circuitry 604 (including clock circuit 605). The digital circuitry (e.g., CMOS, CML, SOS, SOI, BICMOS, PMOS and/or NMOS technology) has a fixed supply voltage ($V_{digital}$) applied thereto from power source 608, which may be any type of electrochemical cell or battery suitable for use in an implantable medical device and providing the appropriate voltage. Some examples of such batteries or cells finding application in respect of the present invention include, but are not limited to, lithium iodine, lithium manganese, nickel cadmium, nickel metal hydride, zinc manganese oxide, zinc silver oxide, zinc mercuric oxide, lithium silver vanadium oxide, lithium ion, divalent silver oxide and silver oxide electrochemical cells or batteries. At least some of the foregoing chemical systems may require stepping down of voltage.

Fixed supply voltage $V_{digital}$ applied for operation of the digital circuitry is kept love to reduce power consumption as previously described herein. Power consumed by the CMOS, CML, SOS, SOI, BICMOS, PMOS and/or NMOS circuitry, for example, is proportional to the square of the supply voltage. Therefore, a lower supply voltage is necessary to reduce power consumption.

In implantable devices, however, designing analog circuitry 602 to function at such low supply voltages is often difficult due to various considerations, such as small circuit headroom, small signal amplitudes (which may effectively reduce amplifier sensitivity), small signal-to-noise ratios, reduced common mode rejection ratios (CMRR), reduced transmitted telemetry power, voltage regulation and current source problems, and the like.

As such, and in accordance with the present invention, device 600 further most preferably includes voltage generator circuit 606 to generate at least one fixed supply voltage ($V_{analog}$) for application to analog circuitry 602. Voltage generator circuit 606 is supplied with supply voltage $V_{digital}$ to generate supply $V_{analog}$. Voltage generator circuit 606 may generate any number of predetermined or fixed voltages greater than $V_{digital}$ to supply different analog circuits. For example, output circuits may require a larger voltage than other amplification circuits. Voltage generator circuit 606 will generate both +/− supplies, ($V_{DD}$ and $V_{SS}$) to power only the analog circuitry 602. $V_{digital}$ circuitry 604 is supplied with the lower voltage $V_{digital}$. For example, as contemplated in the present invention, lower fixed or predetermined supply voltage $V_{digital}$ is in the range of about 1.1 to about 1.6 volts at the beginning-of-life (BOL), to about 0.8 to about 1.0 volts at end-of-life (EOL). The generated fixed supply voltage $V_{analog}$ is in the range of about +/−3.0 volts to about +/−2.0 volts.

Level shifter 610 may be used to translate logic and/or control signals between the analog circuitry 602 and the digital circuitry 604. Such level shifting may be required due to the difference in supply voltage being applied to the respective digital circuitry 604 and analog circuitry 602.

As described previously above, with reduction in supply voltage ($V_{DD}$), threshold voltage ($V_T$) for the circuits is also reduced. With use of lower threshold levels due to lower supply voltages, static power consumption losses undesirably increase by several orders of magnitude. A back gate bias source 609 may therefore be used to provide back gate bias voltages to digital circuitry 604. In this manner, static leakage current losses can be minimized because the equivalent higher threshold voltage has been restored. The back gate bias voltage may be provided by, for example, a fixed voltage source (e.g., a charge pump) connected to the back gate well via a contact. Alternatively, an active body bias scheme whereby the voltage source is selectable or adjustable over an appropriate range may be used. Back gate voltages may be applied in any known manner, such as those previously described herein.

Figure 13:
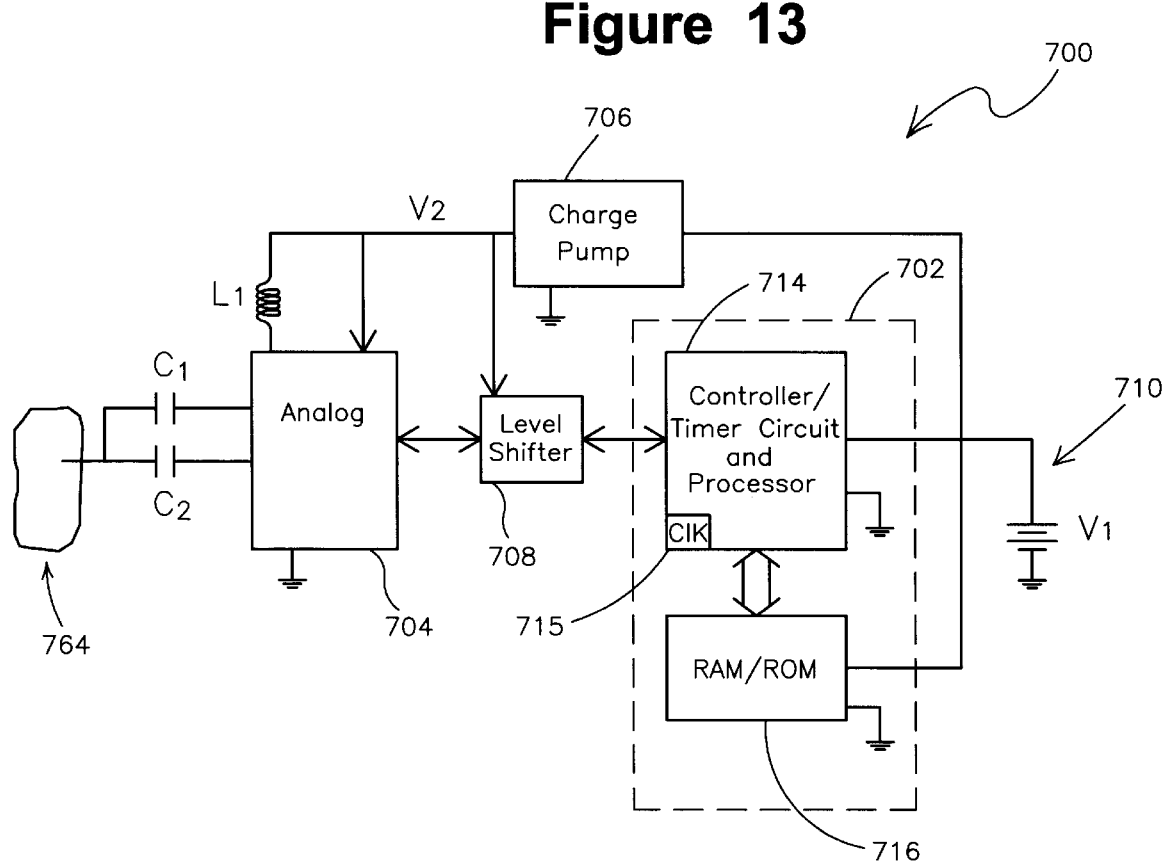
FIG. 13 is a more detailed schematic block diagram of one embodiment of a pacemaker much like that shown in FIG. 9 according to the present invention wherein a lower supply voltage is applied to the digital circuits of the pacemaker with a charge pump being used to generate a higher supply voltage to be applied to the analog circuits of the pacemaker.

FIG. 13 is a more detailed schematic block diagram of one embodiment of pacemaker 700 much like that shown in FIG. 9. According to the present invention, a lower supply voltage V1 (e.g., 1.1 volt source 710) is applied to digital circuitry 702 of pacemaker 700 with charge pump circuit 706 being used to generate at least one higher supply voltage V2 (e.g., 3.0 volts) to be applied to analog circuitry 704 of pacemaker 700.

Digital circuitry 702 may, for example, include circuits such as those described above in reference to pacemaker 300 and FIG. 13. Digital circuitry 702 may include, for example, controller/timer and processor circuit 714 (including a clock circuit 715) or memory circuits such as RAM/ROM circuits 716 for communication with controller/timer and processor circuit 714. Such components and functionality are described herein with reference to FIG. 9.

Analog circuitry 704 may include the analog circuits of pacemaker 300 described previously in reference to FIG. 9. Such analog circuits may include, for example, atrial and ventricular sense amplifiers for receiving A-sense signals from the atrium of heart 764 and for receiving V-sense signals from the ventricle of heart 764. Such sense amplifier circuits are coupled to leads extending to heart 764 via capacitors C1 and C2 to receive the V-Sense (ventricular sense) and A-Sense (atrial sense) signals from heart 764. Sense amplifier circuits then communicate an A-event signal to controller 714 when an atrial event (i.e., an intrinsic atrial event or P-wave) is detected, and communicate a V-event signal to controller 714 when a ventricular event (an intrinsic R-wave) is detected. Analog circuitry 704 may also include bandpass filters and detection circuitry to accomplish such detection. Moreover, analog circuitry 704 may include circuitry for T-wave detection, such as a T-wave amplifier, bandpass filter, or capture detection circuitry.

Analog circuitry 704 may include various other circuits, such as analog to digital (converters (ADCs); voltage reference and current source circuits; telemetry transmission and reception circuitry; sensor amplification circuitry, and bandpass, detection, and drive circuitry to be used with such sensors (e.g., minute ventilation activity, pressure, temperature, pH, pCO2 or oxygen sensors); ECG amplifiers and bandpass filters, such as amplifiers for A-sense signals, V-sense signals and T-wave signals to be used for telemetry purposes; output circuits and pump circuits such as those described in U.S. Pat. No. 5,387,228 to Shelton; battery monitor circuits; power on reset circuits; and any circuits generally designed as analog circuits.

Figure 14:
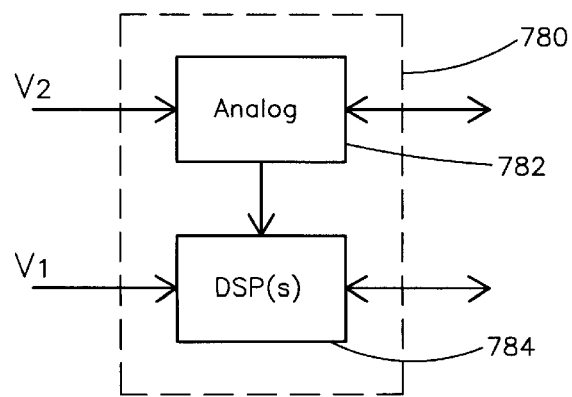
FIG. 14 is a block diagram illustrating the use of digital signal processor(s) in the embodiment shown in FIG. 13.

FIG. 14 shows an alternative embodiment for at least some of the analog circuitry 704 described in reference to FIG. 13. The functions of some of the analog circuits, for example sense amplifiers, may be implemented using circuitry 780 which includes analog circuits 782 (e.g., preamplifiers, ADC's, etc.) and further includes one or more digital signal processors (DSPs) 784 to perform analysis with respect to data communicated thereto by way of analog circuits 782. A similar illustrative implementation is described hereinabove in respect of FIG. 11. As such, and according to the present invention as described in reference to FIGS. 12 through 14, supply voltage V1 is applied to DSP(s) 784 while charge pumped voltage V2 is used as the supply voltage for analog circuits 782. Charge pump circuit 706 is used to generate both +/- voltage supplies ($V_{DD}$ and $V_{SS}$) to power analog circuitry 704. Various configurations for charge pump circuit 706 may be used. Charge pump circuit 706 may be implemented, for example, using the techniques described in U.S. Pat. No. 5,387,228 to Shelton. Charge pump circuit 706 may, for example, be regulated, such as with use of a charge comparator circuit to regulate the voltage, or charge pump circuit 706 may be unregulated. The unregulated voltage may vary as the voltage source V1 varies due to low battery conditions, for example. Yet further, one or more supply voltages may be output from charge pump circuit 706 as voltage V1 is pumped to different amplitudes. More than one supply voltage may be provided by charge pump circuit 706 or more than one charge pump circuit 706 may be employed to provide multiple supply voltages, where each charge pumped voltage is greater than supply voltage V1. That is, one charge pumped voltage may exceed another charged pumped voltage. supply voltages V1 and V2 described in reference to FIG. 13 (i.e., wherein different supply voltages are applied to analog circuitry and digital circuitry, respectively) are fixed predetermined voltages. In other words, pumped predetermined fixed voltage V2 is applied to the analog circuits whenever they are in operation, as opposed to a pumped voltage being applied to circuits only when low battery conditions are apparent. Such voltages are determined at the time the circuits are designed and do not vary other than possibly when batteries have even lower states of charge.

Additionally, pacemaker 700 may include a level shifter 708. Level shifter 708 may be used to translate logic and/or control signals between analog circuitry 704 and controller and processor 714. Such level shifting may be required due to the difference in supply voltages being applied to digital circuitry 702 and analog circuitry 704, respectively. Such a voltage level shifter may be implemented in various configurations. For example, illustrative voltage level shifters are described in U.S. Pat. No. 4,663,701, hereby incorporated by reference herein in its entirety.

Those skilled in the art will now recognize that the technique of applying a lower supply voltage to digital circuitry of a device having a relatively large charged pumped voltage applied to the analog circuitry thereof may be applicable to other medical or implantable devices in a manner similar to that described in reference to a pacemaker. Application of different voltages to the analog and digital circuitry of the PCD described hereinabove in respect of FIG. 10, for example, may be employed to reduce power consumption.

The present invention is compatible with various fabrication technologies, including but not limited to, silicon on insulator (SOI), silicon on sapphire (SOS), current mode logic (CML), BICMOS, PMOS and NMOS technologies, as well as conventional silicon CMOS technologies. U.S. Pat. No. 4,359,653 to Takamasa; U.S. Pat. No. 5,416,043 to Burgener et al.; U.S. Pat. No. 5,538,908 to Kim; U.S. Pat. No. 5,705,421 to Matsushita et al., all hereby incorporated herein by reference, each in its respective entirety, describe integrated circuit fabrication processes and methods of use for at least some of the foregoing integrated circuit types.

The present invention permits devices employing DSPs to perform more functions due to the manner in which power consumption is reduced. Moreover, multiple processor based designs may also be implemented due to reduced power consumption as supply voltages are reduced for the processors.

Additionally, as power consumption is reduced, further functionality may be added to devices in accordance with the present invention to provide a device having added functionality yet lower or the same power consumption relative to conventional prior art devices. A processor in accordance with the present invention may perform, for example, various morphology detection functions such as differentiation of retrograde P-waves and antegrade P-waves of EGM waveform; differentiation of P-waves from far field R-waves; differentiation of AF-A flutter-AT from sinus tachycardia; differentiation of VT-VF-V flutter from SVT; differentiation of cardiac signals from electromagnetic interference; etc. Also by way of example, various embodiments of the present invention may also be employed to detect or filter out electromagnetic interference (EMI) emanating from or generated by theft detectors, conductive signals, RF noise, myopotentials, and the like.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of any particular digital or analog circuits. Furthermore, the voltages applied need not be at any predefined level, but only need be different. Although a charge pump is preferred for generating the higher supply voltage described herein, there may be other voltage generation devices capable of generating the desired voltage levels for application to analog circuits. The present invention is also not limited to use in conjunction with pacemakers or PCDs, but may find further application in other relevant areas such as personal computing or telecommunications where low power consumption is desired. The present invention further includes within its scope the use of other techniques described herein in conjunction with the application of different supply voltages to analog and digital circuits (such as, for example, just-in-time clocking devices and methods).

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination.

I claim:

1. A medical device, comprising:
   one or more analog circuits operable to perform at least one function;
   one or more digital circuits operable to perform at least one function;
   a power source for applying a first fixed supply voltage to the one or more digital circuits; and
   a voltage generation circuit having the first fixed supply voltage supplied thereto, wherein the voltage generation circuit generates at least a second fixed supply voltage for application to the one or more analog circuits, and further wherein the second fixed supply voltage is greater than the first fixed supply voltage.

2. The device of claim 1, wherein the voltage generation circuit is a charge pump circuit for generating the second fixed supply voltage based on the first fixed supply voltage.

3. The device of claim 2, wherein the first supply voltage ranges between about 0.8 volts and about 1.5 volts.

4. The device of claim 2, wherein the second supply voltage ranges between about +/–2.0 volts and about +/–3.0 volts.

5. The device of claim 1, wherein the device further includes means for adjusting the back gate bias of at least one of the one or more digital circuits.

6. The device of claim 1, wherein the one or more digital circuits include at least one of a processor, a controller and a memory.

7. The device of claim 6, wherein the one or more analog circuits include at least one of an atrial sense amplifier, a ventricular sense amplifier, a T-wave amplifier, one or more bandpass filters, one or more detection circuits, one or more sensor amplification circuits, one or more physiological signal amplification circuits, one or more output circuits, a battery monitor circuit, and a power on reset circuit.

8. The device of claim 1, wherein the one or more digital circuits include at least one digital signal processor having the first supply voltage applied thereto receiving data representative of one or more analog signals.

9. The device of claim 1, wherein the one or more analog circuits include at least ore amplifier circuit for amplifying the one or more analog signals.

10. The device of claim 1, wherein the device further includes a level shifter to translate signals between the one or more analog circuits and the one or more digital circuits.

11. The device of claim 1, wherein the device is an hermetically sealed implantable medical device.

12. The device of claim 11, wherein the implantable medical device is selected from the group consisting of an implantable stimulator, an implantable nerve stimulator, an implantable pacemaker, an IPG, an implantable cardioverter, an implantable PCD, an implantable defibrillator, an implantable ICD and an implantable drug pump.

13. The device of claim 1, wherein at least one of the one or more analog circuits comprises circuits of a type selected from the group consisting of CMOS circuits CML circuits, SOS circuits, SOI circuits, BICMOS circuits, PMOS circuits and NMOS circuits.

14. A method for conserving power for a medical device, the method comprising the steps of:
   providing one or more analog circuits of the medical device;
   providing one or more digital circuits of the medical device;
   applying a first fixed supply voltage to the one or more digital circuits; and
   generating a second fixed supply voltage for application to the one or more analog circuits using the first fixed supply voltage, wherein the second fixed supply voltage is greater than the first fixed supply voltage.

15. The method of claim 14, wherein the step of generating the second fixed supply voltage includes the step of generating the second fixed supply voltage using a charge pump circuit.

16. The method of claim 14, wherein the first fixed supply voltage ranges between about 0.8 volts and about 1.5 volts.

17. The method of claim 14, wherein the second fixed supply voltage ranges between about +/–2.0 volts and about +/–3.0 volts.

18. The method of claim 14, wherein the method further includes the step of adjusting the back gate bias of at least one of the one or more digital circuits.

19. The method of claim 14, wherein the step of providing the one or more digital circuits includes providing at least one of a processor, a controller and a memory.

20. The method of claim 14, wherein the step of providing the one or more analog circuits includes the step of providing at least one of an atrial sense amplifier, a ventricular sense amplifier, a T-wave amplifier, one or more bandpass filters, one or more detection circuits, one or more sensor amplification circuits, one or more physiological signal amplification circuits, one or more output circuits, a battery monitor circuit, and a power on reset circuit.

21. The method of claim 14, wherein the step of providing the one or more digital circuits includes the step of providing at least one digital signal processor having the first supply voltage applied thereto for receiving data representative of one or more analog signals.

22. The method of claim 14, wherein the step of providing the one or more analog circuits includes the step of providing at least one amplifier circuit for amplifying the one or more analog signals.

23. The method of claim 14, wherein the method further includes the step of translating the voltage levels of signals being communicated between the one or ore analog circuits and the one or more digital circuits.

24. The method of claim 14, further comprising the step of providing an hermetically sealed implantable medical device.

25. The method of claim 24, wherein the implantable medical device providing step further comprises the step of providing an implantable medical device selected from the group consisting of an implantable stimulator, an implantable nerve stimulator, an implantable pacemaker, an IPG, an implantable cardioverter, an implantable PCD, an implantable defibrillator, an implantable ICD and an implantable drug pump.

26. The method of claim 14, wherein the step of providing the one or more analog circuits further comprises the step of providing circuitry of a type selected from the group consisting of CMOS circuits, CML circuits, SOS circuits, SOI circuits BICMOS circuits, PMOS circuits and NMOS circuits.

* * * * *

UNITED STATES PATENT AND TRADEMARK OFFICE
CERTIFICATE OF CORRECTION

PATENT NO. : 6,091,987

DATED : JULY 18, 2000

INVENTOR(S) : THOMPSON

It is certified that error appears in the above-identified patent and that said Letters Patent is hereby corrected as shown below:

Col. 22, line 63, claim 23: "ore analog" should read --more analog--

Signed and Sealed this

Tenth Day of April, 2001

Attest:

NICHOLAS P. GODICI

Attesting Officer     Acting Director of the United States Patent and Trademark Office